(12) United States Patent
Yun

(10) Patent No.: US 9,889,234 B2
(45) Date of Patent: Feb. 13, 2018

(54) SCAFFOLD FOR HARD TISSUE REGENERATION CONTAINING ACTIVE INGREDIENT FOR TREATING OSTEOPOROSIS AND PREPARING METHOD THEREOF

(71) Applicant: KOREA INSTITUTE OF MACHINERY AND MATERIALS, Daejeon (KR)

(72) Inventor: Hui-suk Yun, Changwon-si (KR)

(73) Assignee: Korea Institute of Machinery and Materials, Daejeon (KR)

(*) Notice: Subject to any disclaimer, the term of this patent is extended or adjusted under 35 U.S.C. 154(b) by 43 days.

(21) Appl. No.: 14/952,471

(22) Filed: Nov. 25, 2015

(65) Prior Publication Data
US 2016/0158416 A1    Jun. 9, 2016

Related U.S. Application Data

(63) Continuation-in-part of application No. PCT/KR2014/011778, filed on Dec. 3, 2014.

(30) Foreign Application Priority Data

Dec. 3, 2014    (KR) .................. 10-2014-0172116

(51) Int. Cl.
| | | |
|---|---|---|
| *A61K 31/00* | (2006.01) | |
| *A61L 27/54* | (2006.01) | |
| *B33Y 10/00* | (2015.01) | |
| *B33Y 40/00* | (2015.01) | |
| *B33Y 70/00* | (2015.01) | |
| *B33Y 80/00* | (2015.01) | |
| *B28B 1/00* | (2006.01) | |
| *A61L 27/12* | (2006.01) | |

(52) U.S. Cl.
CPC ............... *A61L 27/54* (2013.01); *A61L 27/12* (2013.01); *B28B 1/001* (2013.01); *B33Y 10/00* (2014.12); *B33Y 40/00* (2014.12); *B33Y 70/00* (2014.12); *B33Y 80/00* (2014.12); *A61L 2300/112* (2013.01); *A61L 2430/00* (2013.01); *A61L 2430/02* (2013.01)

(58) Field of Classification Search
CPC ........... A61K 6/06; A61K 33/06; A61K 31/05
See application file for complete search history.

(56) References Cited

U.S. PATENT DOCUMENTS

| | | | |
|---|---|---|---|
| 7,163,651 B2 | 1/2007 | Chern Lin | |
| 2008/0241211 A1 | 10/2008 | Han | |
| 2013/0273135 A1* | 10/2013 | Brooks | A61L 27/34 424/426 |
| 2014/0296329 A1* | 10/2014 | Tam | A61K 31/353 514/456 |

FOREIGN PATENT DOCUMENTS

| | | | |
|---|---|---|---|
| KR | 10-2010-0026910 A | | 3/2010 |
| KR | 10-2013-0028406 A | | 3/2013 |
| WO | WO 2009/035265 | * | 3/2009 |

OTHER PUBLICATIONS

Bose, Susmita, and Solaiman Tarafder. "Calcium phosphate ceramic systems in growth factor and drug delivery for bone tissue engineering: a review." Acta biomaterialia 8.4 (2012): 1401-1421.

* cited by examiner

*Primary Examiner* — Ruth A Davis
(74) *Attorney, Agent, or Firm* — Klarquist Sparkman, LLP

(57) ABSTRACT

A scaffold for hard tissue regeneration comprising an active ingredient for treating osteoporosis and a preparation method thereof. The scaffold for hard tissue regeneration is prepared by the steps of mixing a polyphenol-based natural substance containing Quercetein or Genistein involved in the activation of osteoblasts and osteoclasts and the biofunctional analog thereof with a ceramic scaffold material and molding the mixture at room temperature into a three-dimensional scaffold. The biofunctional material included in the scaffold above may be sustain-released slowly over the long period of time so that the osteoblast activity is directly improved and at the same time the osteoclast activity is suppressed in the course of bone regeneration, to have the effect of improving bone regeneration.

12 Claims, 25 Drawing Sheets

CDHA : Comparative Example 1
$Q_{200}$-CDHA : Example 1
$G_{200}$-CDHA : Example 3
$A_{200}$-CDHA : Comparative Example 2

CDHA : Comparative Example 1
Q₂₀₀-CDHA : Example 1
G₂₀₀-CDHA : Example 3
A₂₀₀-CDHA : Comparative Example 2

SCAFFOLD FOR HARD TISSUE REGENERATION CONTAINING ACTIVE INGREDIENT FOR TREATING OSTEOPOROSIS AND PREPARING METHOD THEREOF

CROSS REFERENCE TO RELATED APPLICATION

This patent application is a continuation-in-part of PCT/KR2014/011788, filed Dec. 3, 2014, which claims the benefit of priority from Korean Patent Application No. 10-2014-0172116, filed on Dec. 3, 2014. The contents of both patent applications are incorporated herein by reference.

BACKGROUND

Field of the Disclosure

The present disclosure relates to a scaffold for hard tissue regeneration comprising an active ingredient for treating osteoporosis and a preparation method thereof.

Description of the Related Art

The average life expectancy has significantly increased due to the rapid economic development and the advancement of medical technology. As a result, the aged population has increased and accordingly the prevalence rate of various degenerative bone diseases including osteoporosis has been increased as well. Osteoporosis is a cause of various bone defects including fracture. To treat osteoporosis, bone graft materials such as bone filler, bone binder, implant, and porous scaffold are needed. Osteoporosis patients demonstrate poorer bone density, bone volume, and bone quality. Thus, when a bone graft material including a general porous scaffold is transplanted, secondary bone damage might be induced owing to the differences of the physical properties. So, a material customized for osteoporosis patients has to be developed. A scaffold can be used in order to induce regeneration of tissue via a self recovering system. The scaffold acts as a bridge connecting the tissues, and thus it has to be designed to be decomposed at the same speed as the bone regeneration. That is, if the bone regeneration occurs faster than the decomposition of the scaffold, the scaffold can hinder the bone regeneration, and if the bone regeneration is slower than the decomposition of the scaffold, that means the scaffold is decomposed before the bone regeneration, the full effect of the scaffold cannot be expected.

In general, the osteoblast activity to make bone is weaker than the osteoclast activity to absorb bone in an osteoporosis patient. Therefore, a porous scaffold developed for normal people does not fit for osteoporosis patients. To bring full effect of the scaffold, it is necessary to increase the osteoblast activity and at the same time to inhibit the osteoclast activity in the transplantation area.

The osteoporosis treating agents used clinically today are largely divided into two groups, which are bone resorption inhibitors and bone forming agents. The bone resorption inhibitor is exemplified by bisphosphonate, female hormone (estrogen), female hormone receptor modulator, and calcitonin. Among these, the bisphosphonate-based drug is most frequently prescribed as the primary drug for treating osteoporosis. However, this drug is apt to be accumulated in the inside of body, so that serious side effects including mandible necrosis can be induced if it is administered for a long term or at a big dose. It has been considered to use a growth factor like BMP (bone morphogenic proteins) that is excellent in inducing bone tissue generation as a bone forming agent, but it is mostly produced in foreign countries by taking advantage of genetic recombination technique and thus it is sold expensive here. That means, medical costs to apply the drug to bone defect caused by osteoporosis is a burden. In the meantime, various food components have been studied not as a treating agent but as a preventive agent or as nutrients efficient for osteoporosis, and they have been orally-administered to prevent osteoporosis. Studies are undergoing in order to increase the efficiency by adding gel or patty type bone filler with the above osteoporosis treating materials (patent reference 1) and by adding such metal ions (zinc, copper, iron, magnesium, silver, and strontium) that bring favorable effect on bone formation to a bone graft material to be released later on.

In particular, the scaffold based on ceramic which is similar in properties to the mineral component of human bone has to be prepared by high temperature sintering considering the characteristics of ceramic process. So, if a drug or a growth factor, which is vulnerable to heat, is used, it has to be added after the high temperature sintering. The method for adding such a material is that a drug or a growth factor dispersed in a solution is adsorbed on the surface of a scaffold. However, this procedure causes early quick release of the drug and makes the long time sustained-release difficult. Besides, the amount of the drug added therein is limited also. Therefore, the method using ceramic mixed with natural or synthetic polymer or added with such metal ions not vulnerable to heat treatment is more general these days. However, the former has a disadvantage of difficulty in expecting good mechanical properties and bio-activity and the latter has a disadvantage of difficulty in introducing enough amount of metal ions or side effects of the metal ions.

To overcome the said disadvantage, patent reference 2 proposed a room temperature processing method of ceramic scaffold. According to this method, a ceramic scaffold can be prepared at room temperature, so that it can include a drug or a growth factor which is vulnerable to heat. Polyphenol, a natural substance which has long been used to prevent osteoporosis, has the effect of promoting the osteoblast activity and the effect of inhibiting the osteoclast activity. However, these effects are expected when it is administered for a long term via oral-administration and there is no case report so far to use this material as an additive to a scaffold or to a bone graft material to increase the local bone regeneration. If it is possible to introduce a natural substance that is effective in controlling osteoblasts and/or osteoclasts into a scaffold even so as to make long time sustained-release of this material possible, it could lead a way to successful preparation of a novel porous scaffold applicable to osteoporosis patient without worry about side effects caused by the conventional bisphosphonate, estrogen, and calcitonin, high costs for growth factor, and difficult process.

Thus, the present inventors continued study on the scaffold for hard tissue regeneration that is applicable to osteoporosis patient. And as a result, the inventors established a method to introduce a polyphenol-based natural substance to a ceramic scaffold evenly, which is represented by Quercetein or Genistein that has less side effects than the conventional osteoporosis treating agent bisphosphonate and can promote the osteoblast activity but inhibit the osteoclast activity so as to increase bone regeneration effect, and further prepared a scaffold for hard tissue regeneration that is suitable for sustained-release of the active ingredient for bone formation, leading to the completion of this invention.

SUMMARY

The disclosed device and method provide a scaffold for hard tissue regeneration comprising an active ingredient for treating osteoporosis and calcium phosphate ceramic.

A preparation method of the scaffold for hard tissue regeneration is also provided.

To achieve the above goals, the present invention provides a scaffold for hard tissue regeneration comprising an active ingredient for treating osteoporosis and calcium phosphate ceramic.

The present disclosure also provides a preparation method of the scaffold for hard tissue regeneration comprising the following steps:

preparing a powder mixture by pulverizing/mixing a solvent, an active ingredient for treating osteoporosis, and calcium phosphate ceramic in ball mill, and drying thereof (step 1);

preparing a paste by mixing the powder mixture prepared in step 1 with a solvent (step 2);

molding the paste prepared in step 2 as a three-dimensional scaffold (step 3); and inducing bone cement reaction by dipping the three-dimensional scaffold prepared in step 3 in a hardening solution (step 4).

Further, the present invention provides a preparation method of the scaffold for hard tissue regeneration comprising the following steps:

preparing calcium phosphate ceramic powder by pulverizing calcium phosphate ceramic (step 1);

preparing a paste by mixing the calcium phosphate ceramic powder prepared in step 1 with an active ingredient for treating osteoporosis in a solvent (step 2);

molding the paste prepared in step 2 as a three-dimensional scaffold (step 3); and inducing bone cement reaction by dipping the three-dimensional scaffold prepared in step 3 in a hardening solution (step 4).

Advantageous Effect

The scaffold for hard tissue regeneration of the present invention is prepared by the steps of mixing a polyphenol-based natural substance containing Quercetein or Genistein involved in the activation of osteoblasts and osteoclasts and the biofunctional analogue thereof with a ceramic scaffold material and molding the mixture at room temperature into a three-dimensional scaffold. At this time, the biofunctional material included in the scaffold above is sustain-released slowly over the long period of time so that the osteoblast activity is directly improved and at the same time the osteoclast activity is suppressed in the course of bone regeneration, to have the effect of improving bone regeneration.

BRIEF DESCRIPTION OF THE DRAWINGS

The application of the preferred embodiments of the present disclosure is best understood with reference to the accompanying drawings, wherein.

DESCRIPTION OF THE PREFERRED EMBODIMENTS

Figure 1:
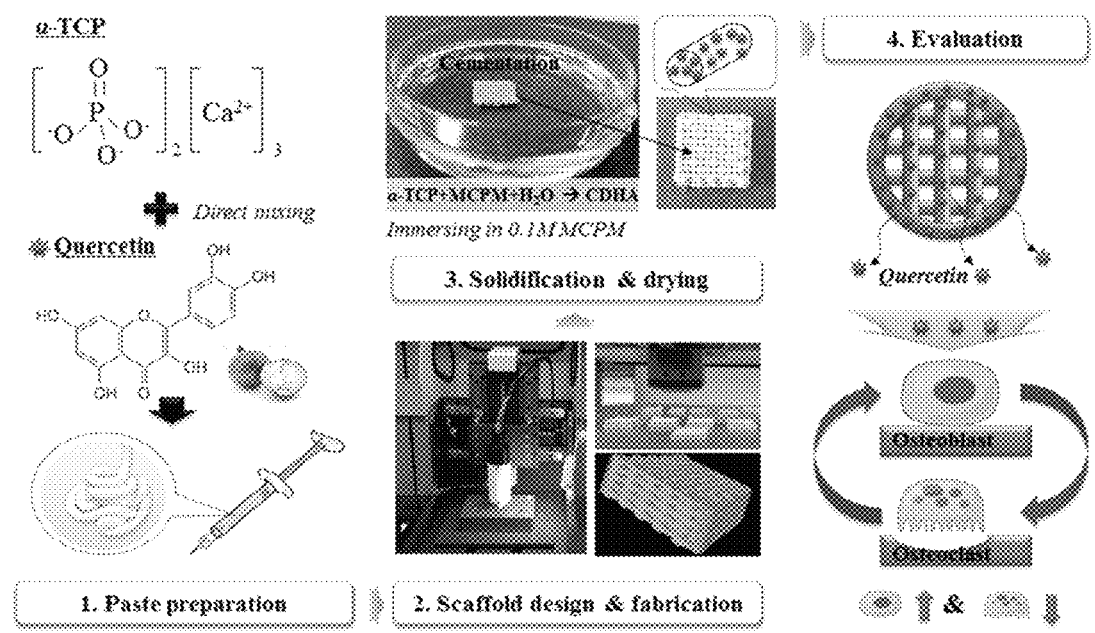
FIG. 1 is a set of images illustrating the preparation process of the scaffold for hard tissue regeneration of the present invention.

Hereinafter, preferred embodiments are described in detail.

A scaffold is provided for hard tissue regeneration comprising an active ingredient for treating osteoporosis and calcium phosphate ceramic. At this time, the active ingredient for treating osteoporosis is characteristically a polyphenol-based natural substance or a bisphosphonate-based drug.

Particularly, the active ingredient for treating osteoporosis is preferably selected from the group consisting of polyphenol-based natural substances such as Quercetein, Genistein, Curcumin, Saurolactam, Sauchinone, Baicalin, Daidzein, Rutin, Anthocyanidin, Fisetin, Icariin, Kaempferol, E. Koreanum Nakei and Equol; or bisphosphonate-based drugs such as alendronate, risedronate, etidronate, clodronate, neridronate, ibandronate, zoledronate and olpadronate, and more preferably Quercetein or Genistein.

The calcium phosphate ceramic herein can be α-TCP (α-Tricalcium phosphate), β-TCP (β-Tricalcium phosphate), Hydroxyapatite, DCPD (Dicalcium phosphate dihydrate), MCPM (Monocalcium phosphate monohydrate), or DCPA (Dicalcium phosphate anhydrous), and more preferably α-TCP (α-Tricalcium phosphate).

It is generally proposed that the scaffold applicable to osteoporosis patient is preferably prepared basically with a polymer material and contains a bisphosphonate-based drug or a growth factor. The scaffold for bone regeneration is basically constructed on ceramic because 70% of human bone is mineral represented by hydroxycarbonateapatite. However in that case, sintering process is required considering the characteristics of ceramic. So, it is also required that the sintered ceramic scaffold is dipped in a solution containing a target drug dispersed therein to adsorb the drug onto the surface of the scaffold. But, with this method, the target drug or the growth factor is only adsorbed on the surface of the scaffold, indicating that it is difficult to control the early release and thus the scaffold might not be usable as a sustained-release scaffold which is constantly active in the course of bone regeneration.

To overcome the above problem, the present inventors prepared a paste by mixing calcium phosphate ceramic with an active ingredient for treating osteoporosis evenly, and performed molding of the mixture into a scaffold. Therefore, the present invention provides a preparation method of the scaffold for hard tissue regeneration which is effective in releasing the active ingredient for treating osteoporosis slowly and constantly when it is introduced in a living body.

More particularly, the present disclosure provides a preparation method of the scaffold for hard tissue regeneration comprising the following steps:

preparing a powder mixture by pulverizing/mixing a solvent, an active ingredient for treating osteoporosis, and calcium phosphate ceramic in ball mill, and drying thereof (step 1);

preparing a paste by mixing the powder mixture prepared in step 1 with a solvent (step 2);

molding the paste prepared in step 2 as a three-dimensional scaffold (step 3); and inducing bone cement reaction by dipping the three-dimensional scaffold prepared in step 3 in a hardening solution (step 4).

Hereinafter, the preparation method of the scaffold for hard tissue regeneration is described in more detail step by step.

In the preparation method of the scaffold for hard tissue regeneration of the invention, step 1 is to prepare a powder mixture by pulverizing/mixing a solvent, an active ingredient for treating osteoporosis, and calcium phosphate ceramic in ball mill, and drying thereof.

At this time, the active ingredient for treating osteoporosis is a hydrophobic polyphenol-based natural substance or a bisphosphonate-based drug.

Particularly, the active ingredient for treating osteoporosis is preferably selected from the group consisting of Quercetein, Genistein, Curcumin, Saurolactam, Sauchinone, Baicalin, Daidzein, Rutin, Anthocyanidin, Fisetin, Icariin, Kaempferol, E. Koreanum Nakei, and Equol, and more preferably Quercetein or Genistein.

The bisphosphonate-based drug herein is preferably selected from the group consisting of alendronate, risedronate, etidronate, clodronate, neridronate, ibandronate, zoledronate, and olpadronate.

The calcium phosphate ceramic herein can be α-TCP (α-Tricalcium phosphate), β-TCP (β-Tricalcium phosphate), Hydroxyapatite, DCPD (Dicalcium phosphate dihydrate), MCPM (Monocalcium phosphate monohydrate), or DCPA (Dicalcium phosphate anhydrous), and more preferably α-TCP (α-Tricalcium phosphate).

The solvent herein is exemplified by ionic water, tetrahydrofurane, dioxane, ethylether, 1,2-dimethoxyethane, methanol, ethanol, propanol, butanol, dimethylformamide, dimethylsulfoxide, dichloromethane, and dichloroethane, and more preferably ethanol is used because the hydrophobic polyphenol-based natural substance is more easily dissolved in it.

In the preparation method of the scaffold for hard tissue regeneration of the invention, step 2 is to prepare a paste by mixing the powder mixture prepared in step 1 with a solvent.

At this time, the solvent is exemplified by de-ionized water, PBS (phosphate buffered saline), tetrahydrofurane, dioxane, ethylether, 1,2-dimethoxyethane, methanol, ethanol, propanol, butanol, dimethylformamide, dimethylsulfoxide, dichloromethane, and dichloroethane, and more preferably ethanol is used because the hydrophobic polyphenol-based natural substance is more easily dissolved in it. Herein, the solvent can additionally contain a thickening agent such as hydroxypropyl methyl cellulose (HPMC), gelatin, collagen, and alginate to increase the viscosity of the paste, and herein it contains hydroxypropyl methyl cellulose (HPMC) more preferably.

In the preparation method of the scaffold for hard tissue regeneration of the invention, step 3 is to mold the paste prepared in step 2 as a three-dimensional scaffold.

At this time, the molding of the paste is preferably performed by additive manufacturing method, and this method can be controlled by the computer system as presented below.

Particularly, the additive manufacturing method uses gantry robotic deposition apparatus equipped with an actuator to control the location of a deposition nozzle to prepare the three-dimensional scaffold. This system enables three-dimensional motion control (x-axis, y-axis, and z-axis) and a syringe is attached on the z-axis motion stage (see FIG. 1).

In the preparation method of the scaffold for hard tissue regeneration of the invention, step 4 is to induce bone cement reaction by dipping the three-dimensional scaffold prepared in step 3 in a hardening solution.

At this time, the hardening solution is preferably selected from the group consisting of MCPM (Mono Calcium Phosphate Mono Hydrate), $H_2O$, PBS (Phosphate buffer saline), DAHP (Diammonium hydrogen phosphate), $NH_4H_2PO_4$, $KH_2PO_4$, $K_2HPO_4$, and $NaH_2PO_4$, and more preferably MCPM (Mono Calcium Phosphate Mono Hydrate) is used herein.

In the preparation method of the scaffold for hard tissue regeneration of the invention, an additional step of improving the mechanical properties of the scaffold by dipping the three-dimensional scaffold prepared in step 4 in de-ionized water (step 5) can be included.

At this time, the improvement of the mechanical properties in this invention is characteristically achieved by dipping the three-dimensional scaffold prepared in step 4 in de-ionized water so as to induce additional bone cement reaction.

The present disclosure also provides a preparation method of the scaffold for hard tissue regeneration comprising the following steps:

preparing calcium phosphate ceramic powder by pulverizing calcium phosphate ceramic (step 1);

preparing a paste by mixing the calcium phosphate ceramic powder prepared in step 1 with an active ingredient for treating osteoporosis in a solvent (step 2);

molding the paste prepared in step 2 as a three-dimensional scaffold (step 3); and inducing bone cement reaction by dipping the three-dimensional scaffold prepared in step 3 in a hardening solution (step 4).

Hereinafter, the preparation method of the scaffold for hard tissue regeneration of the invention is described in more detail step by step.

In the preparation method of the scaffold for hard tissue regeneration of the invention, step 1 is to prepare calcium phosphate ceramic powder by pulverizing calcium phosphate ceramic.

At this time, the mean particle size of the powder is preferably 1~50 μm and more preferably 2~25 μm, and most preferably 3~6 μm. The particle size is related to the size of the nozzle used for the preparation of the scaffold. As the size of the nozzle gets smaller, the particle size has to be smaller in order for the paste to be extruded without clogging. When the ceramic powder is mixed with the active ingredient for treating osteoporosis, it is preferred for these two ingredients to be similar in size for well, even mixing. Specifically, the mean particle size of Quercetein is 4 μm and the mean particle size of Genistein is 5 μm. Thus, the preferable particle size of the ceramic powder is 3~6 μm.

In the preparation method of the scaffold for hard tissue regeneration of the invention, step 2 is to prepare a paste by mixing the calcium phosphate ceramic powder prepared in step 1 with an active ingredient for treating osteoporosis in a solvent.

At this time, the active ingredient for treating osteoporosis is a hydrophobic polyphenol-based natural substance or a bisphosphonate-based drug.

Particularly, the polyphenol-based natural substance is preferably selected from the group consisting of Quercetein, Genistein, Curcumin, Saurolactam, Sauchinone, Baicalin, Daidzein, Rutin, Anthocyanidin, Fisetin, Icariin, Kaempferol, E. Koreanum Nakei, and Equol, and more preferably Quercetein or Genistein.

The bisphosphonate-based drug herein is preferably selected from the group consisting of alendronate, risedronate, etidronate, clodronate, neridronate, ibandronate, zoledronate, and olpadronate.

The calcium phosphate ceramic herein can be α-TCP (α-Tricalcium phosphate), β-TCP (β-Tricalcium phosphate), Hydroxyapatite, DCPD (Dicalcium phosphate dihydrate), MCPM (Monocalcium phosphate monohydrate), or DCPA (Dicalcium phosphate anhydrous), and more preferably α-TCP (α-Tricalcium phosphate).

At this time, the solvent is exemplified by de-ionized water, PBS (phosphate buffered saline), tetrahydrofurane, dioxane, ethylether, 1,2-dimethoxyethane, methanol, ethanol, propanol, butanol, dimethylformamide, dimethylsulfoxide, dichloromethane, and dichloroethane, and more preferably ethanol is used because the hydrophobic polyphenol-based natural substance is more easily dissolved in it. Herein, the solvent can additionally contain a thickening agent such as hydroxypropyl methyl cellulose (HPMC), gelatin, collagen, and alginate to increase the viscosity of the paste, and herein it contains hydroxypropyl methyl cellulose (HPMC) more preferably.

Further, since the active ingredient for treating osteoporosis is an organic substance, there is a risk of thermal denaturation at high temperature. So, the mixing temperature is preferably room temperature in order to prevent any change of mechanical properties of the active ingredient for treating osteoporosis.

In the preparation method of the scaffold for hard tissue regeneration of the invention, step 3 is to mold the paste prepared in step 2 as a three-dimensional scaffold.

At this time, the molding of the paste is preferably performed by additive manufacturing method, and this method can be controlled by the computer system as presented below.

Particularly, the additive manufacturing method uses gantry robotic deposition apparatus equipped with an actuator to control the location of a deposition nozzle to prepare the three-dimensional scaffold. This system enables three-dimensional motion control (x-axis, y-axis, and z-axis) and a syringe is attached on the z-axis motion stage (see FIG. 1).

In the preparation method of the scaffold for hard tissue regeneration of the invention, step 4 is to induce bone cement reaction by dipping the three-dimensional scaffold prepared in step 3 in a hardening solution.

At this time, the hardening solution is preferably selected from the group consisting of MCPM (Mono Calcium Phosphate Mono Hydrate), $H_2O$, PBS (Phosphate buffer saline), DAHP (Diammonium hydrogen phosphate), $NH_4H_2PO_4$, $KH_2PO_4$, $K_2HPO_4$, and $NaH_2PO_4$, and more preferably MCPM (Mono Calcium Phosphate Mono Hydrate) is used herein.

In the preparation method of the scaffold for hard tissue regeneration of the invention, an additional step of improving the mechanical properties of the scaffold by dipping the three-dimensional scaffold prepared in step 4 in de-ionized water (step 5) can be included.

At this time, the improvement of the mechanical properties in this invention is characteristically achieved by dipping the three-dimensional scaffold prepared in step 4 in de-ionized water so as to induce additional bone cement reaction.

The scaffold for hard tissue regeneration of the present invention uses a polyphenol-based natural substance instead of a bisphosphonate-based drug, the conventional osteoporosis treating agent, so that it has less worry of side effects and can promote the osteoblast activity but suppress the osteoclast activity. In addition, Quercetein or Genistein, which is expected to bring an improved bone regeneration effect, is evenly introduced in the scaffold at room temperature, indicating the long time sustained-release of the active ingredient is expected. To confirm this, the following experiment was performed.

First, the release characteristics of Quercetein or Genistein included in the scaffold for hard tissue regeneration of the present invention was evaluated. As a result, Quercetein was 100% sustained-released over 40 days in ethanol, the dissolving solvent, without early acute releasing in the whole experimental period of 60 days. To monitor the in vitro release, the release of Quercetein in de-ionized water and PBS (Phosphate buffered saline) was observed. As a result, Quercetein was released 10% in the early 20 days and 50% over 60 days.

In the meantime, Genistein was 100% released in the early 5 days in ethanol, the dissolving solvent. To monitor in vitro release, the release of Genistein in de-ionized water and PBS (Phosphate buffered saline) was observed. As a result, Genistein was sustained-released 60% over 55 days without early acute releasing (see FIGS. 2 and 3 of Experimental Example 1).

The following experiment was performed to investigate the changes of the osteoblast proliferation activity according to the concentrations of the target drug. As a result, as the concentration of Quercetein increased, the proliferation of osteoblasts increased. Particularly, when the concentration of Quercetein was increased to 1~200 µM, the proliferation of osteoblasts was increased dose-dependently. When the concentration of Genistein was increased to 1~10 µM, the proliferation of osteoblasts was also increased. However, when the concentration of Genistein was increased more than 10 µM, the proliferation of osteoblasts was rather inhibited (see FIGS. 4 and 5 of Experimental Example 2).

In general, in order to compare the pharmaceutical effect of the polyphenol-based natural substance used to be added to food or nutritional supplements with that of the conventional osteoporosis treating agent Alendronate, equal amounts of these materials were added to test samples, followed by investigation of the effect of each material on osteoblasts and osteoclasts. As a result, both Quercetein and Genistein demonstrated similar or better effect than that of Alendronate on osteoblasts. Particularly, Genistein demonstrated similar effect to Alendronate at the concentration of 200 µM. In the meantime, Quercetein demonstrated a significantly improved effect, that is Quercetein increased the proliferation of osteoblasts, compared with Alendronate on day 3 and day 5. Both Quercetein and Genistein demonstrated the promoting effect on the proliferation at the concentration of 1 µM on day 3 and day 5, and at this time the effect by Genistein was more significant. That is, it was confirmed by the above experiment that the natural substance had similar or better effect in promoting the differentiation of osteoblasts, compared with Alendronate, the conventional osteoporosis treating agent (see FIG. 6 of Experimental Example 2).

How the active ingredient included in the scaffold for hard tissue regeneration of the invention could affect the proliferation of osteoblasts while being sustained-released was investigated. As a result, the scaffold contained 200 µM Quercetein and 1 µM Genistein significantly increased the osteoblast proliferation activity, compared with the scaffold not added with such drugs (see FIG. 7 of Experimental Example 2).

The effects of Quercetein, Genistein and Alendronate on the proliferation of osteoclasts were compared. As a result, all of them inhibited the proliferation of osteoclasts. In particular, when treated at the same concentration, 200 µM Quercetein and 1 µM Genistein demonstrated greater inhibitory effect than Alendronate. That is, these natural substances had similar or greater inhibitory effect on the differentiation of osteoclasts than Alendronate, the conventional drug (see FIG. 8 of Experimental Example 3).

The changes of the osteoclast proliferation activity according to the concentration of the active ingredient included in the scaffold for hard tissue regeneration of the invention were examined. As a result, compared with the scaffold for hard tissue regeneration that did not contain Quercetein, the scaffold for hard tissue regeneration containing Quercetein at the concentrations of 1 µM and 200 µM was confirmed to inhibit efficiently the proliferation of osteoclasts. When the scaffold contained Quercetein at the concentration of 200 µM, the effect was greater. The scaffold for hard tissue regeneration containing Genistein at the concentrations of 1 µM and 200 µM respectively was also compared with the scaffold for hard tissue regeneration that did not contain Genistein. As a result, the scaffold containing Genistein at the concentrations of 1 µM and 200 µM was confirmed to inhibit efficiently the proliferation of osteoclasts. When the scaffold contained Genistein at the concentration of the inhibitory effect was greater (see FIGS. 9 and 10 of Experimental Example 3).

Further, the early differentiation of osteoblasts was investigated by observing the changes of alkaline phosphatase activity. As a result, compared with the scaffold that did not contain the active ingredient, the scaffold for hard tissue regeneration containing 200 µM of Quercetein or 1 µM of Genistein was confirmed to improve the early differentiation of osteoblasts by activating alkaline phosphatase activity significantly (see FIG. 11 of Experimental Example 4).

To observe the effect on the osteogenic differentiation of osteoblasts of Quercetein or Genistein included in the scaffold for hard tissue regeneration of the present invention, the inventors performed real-time PCR to observe the changes of the early or late factors on the osteogenic differentiation of osteoblasts such as collagen type-I (Col-I), Runx2, alkaline phosphatase (ALP), osteocalcin (OC) and bone sialoprotein (BSP). As a result, when osteoblasts were seeded in the scaffold for hard tissue regeneration prepared in Example 1 or Example 4, the osteogenic differentiation of osteoblasts was promoted over the time, compared with when osteoblasts were seeded in the scaffold for hard tissue regeneration prepared in Comparative Example 1 (FIGS. 12~16 of Experimental Example 5).

The effect of the sustained-release of Quercetein or Genistein included in the scaffold for hard tissue regeneration of the present invention on the bone mineralization was investigated. Compared with the scaffold that did not contain the drugs, when the scaffold containing the drugs were treated, a dark red color was observed, which was attributed to the increase of calcium concentration, confirmed by alizarin red S staining. This result indicates that the bone mineralization was promoted by the scaffold (FIG. 17 of Experimental Example 6).

Figure 18:
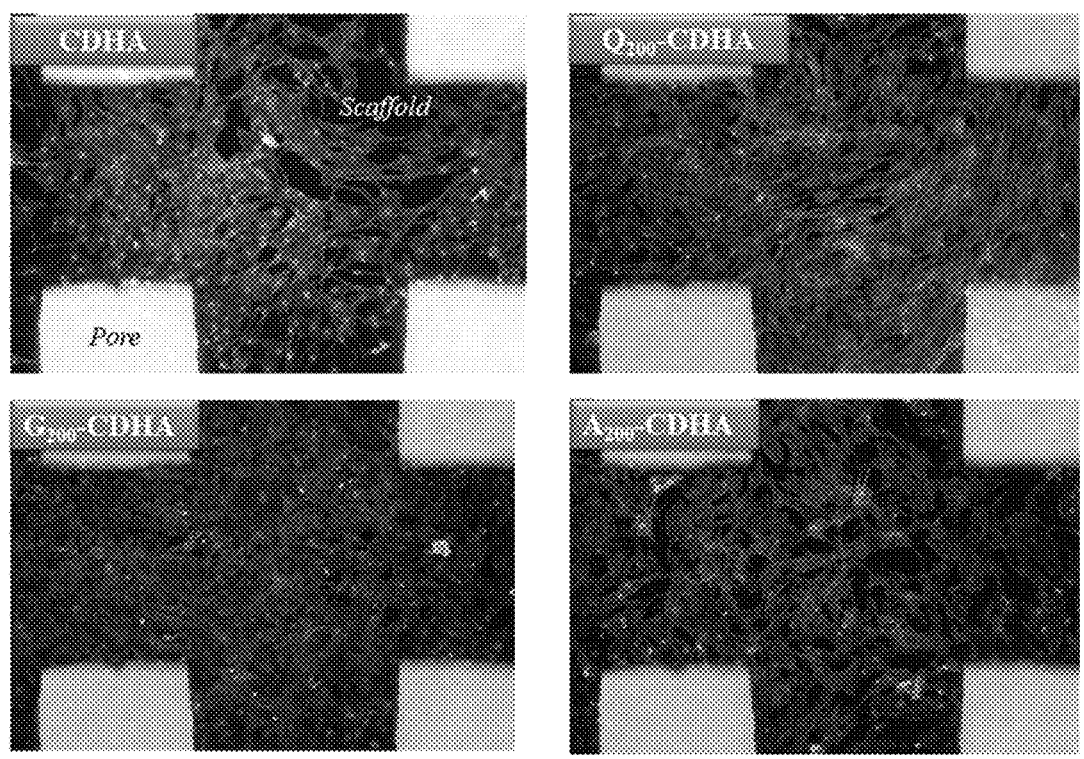
FIG. 18 is a set of images illustrating the proliferation of osteoblasts (MC3T3-E1) in the presence of the medicinal material released from the scaffold for hard tissue regeneration prepared in each of Example 1, Example 3, Comparative Example 1, and Comparative Example 2.
Figure 19:
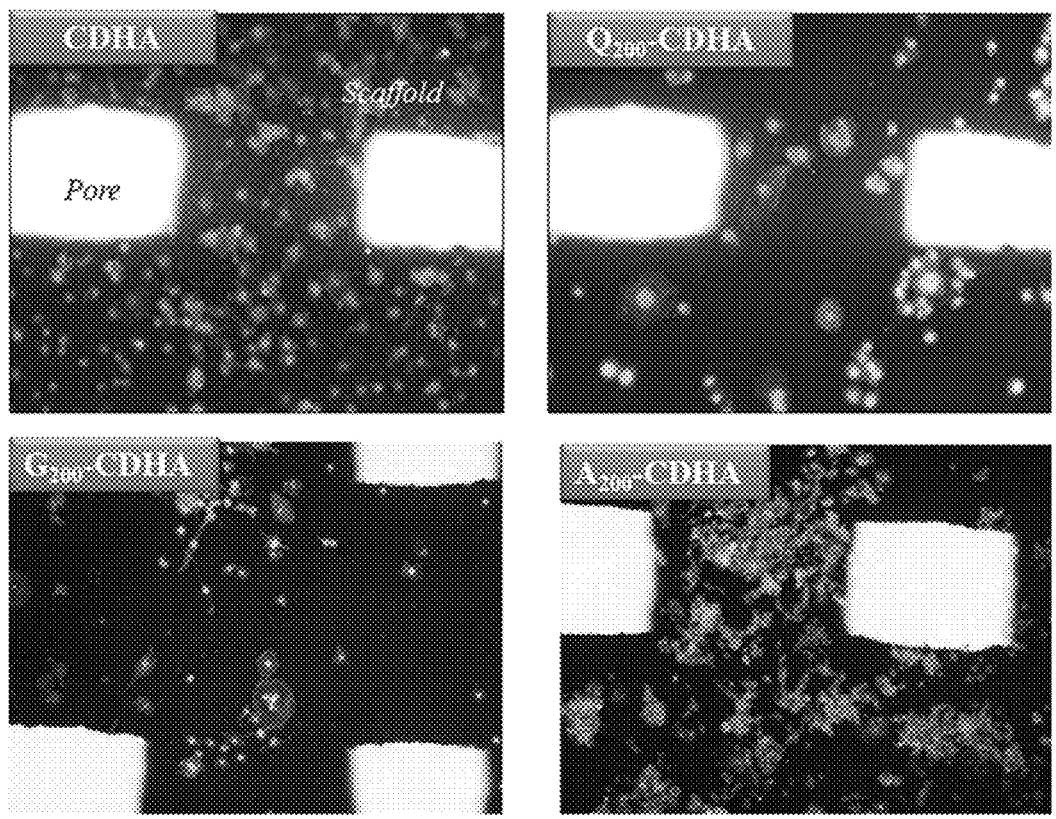
FIG. 19 is a set of images illustrating the proliferation of osteoclasts (RAW 264.7) in the presence of the medicinal material released from the scaffold for hard tissue regeneration prepared in each of Example 1, Example 3, Comparative Example 1, and Comparative Example 2.

The proliferations of osteoblasts and osteoclasts according to the release of the drug included in the scaffold for hard tissue regeneration of the present invention were investigated. As a result, the scaffolds for hard tissue regeneration prepared in Example 1 and Example 3 were confirmed to promote significantly the proliferation of osteoblasts and at the same time inhibit significantly the proliferation of osteoclasts, compared with the scaffolds for hard tissue regeneration prepared in Comparative Example 1 and Comparative Example 2 (FIGS. 18 and 19 of Experimental Example 7).

Further, the mechanical properties of the scaffold for hard tissue regeneration of the present invention were investigated. As a result, the mechanical properties of the scaffolds prepared in Example 1 and Example 3 were not much different from that of Comparative Example 1. In the meantime, the scaffold prepared in Comparative Example 2 containing Alendronate demonstrated poorer mechanical properties than those of the scaffolds of Comparative Example 1 and Examples 1 and 2 (see FIG. 20 of Experimental Example 8).

Cement reaction of the scaffold was examined by XRD (X-ray diffraction) measurement. As a result, hardening into powder like crystal was not observed before the preparation of the scaffold. However, when the scaffold was prepared by using 3D printer and dipped in 0.1 M MCPM (monocalcium phosphate monohydrate), phase transition from α-TCP (α-Tricalcium phosphate) into CDHA (Calcium Deficient Hydroxyapatite) progressed and at last complete phase transition into CDHA was achieved by additional dipping in de-ionized water (see FIG. 21 of Experimental Example 9).

The biodegradability of the scaffold for hard tissue regeneration of the present invention with or without containing the said drug was evaluated. As a result, the Biodegradability of the scaffold for hard tissue regeneration prepared in Example 1 containing Quercetein was similar to that of the scaffold prepared in Comparative Example 1 that did not contain Quercetein (see FIG. 22 of Experimental Example 22).

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Scaffold for Hard Tissue Regeneration (Containing 200 μM Quercetein)

Step 1: Preparation of α-TCP (α-Tricalcium Phosphate) Powder

Calcium carbonate ($CaCO_3$) and dicalcium phosphate ($CaHPO_4$) were reacted at the molar ratio of 1:2, followed by mixing physically to prepare a powder mixture. To mix them well, ethanol was used as a solvent and rolling mill was performed for 24 hours. 24 hours later, the obtained slurry was dried and filtered with 100 μM sieve. The powder proceeded to sintering at 1400° C. for 12 hours, followed by quenching at 1400° C. To reduce the particle size, the mixture in ethanol was treated in ball mill at 250 rpm for 4 hours. Then, the powder was dried and filtered with 25 μm sieve. The particle size distribution of α-TCP prepared above was investigated by using Beckman cutler Machine. As a result, the mean particle size was confirmed to be 4.8 μm.

Step 2: Preparation of Extruded Paste for the Preparation of Scaffold for Hard Tissue Regeneration Containing 200 μM of Quercetein To prepare the extruded paste, a certain amount of Quercetein was added to the α-TCP powder prepared in step 1, followed by ball-milling to induce even distribution. As a result, the powder mixture was prepared. At this time, 200 μM of Quercetein was mixed with each scaffold. 1% hydroxypropyl methyl cellulose (HPMC, Sigma) dissolved in 30% ethanol was added thereto at the ratio of 1:0.5, which was then well-mixed to prepare a paste. If necessary, the drug can be directly dissolved in HPMC solution to prepare a paste.

Step 3: Preparation of Scaffold for Hard Tissue Regeneration Containing 200 μM of Quercetein The calcium phosphate scaffold which has not been harden yet was prepared from the green paste obtained in step 2 by using paste extrusion deposition (PED) system among the additive manufacturing methods. The green paste containing Quercetein (200 μM/scaffold) was loaded in a syringe for PED system as shown in FIG. 1.

The green paste loaded in the syringe was let go through the nozzle and molded as a three-dimensional scaffold by PED system. At this time, the shape and the size of the scaffold prepared thereby were regulated by computer system.

Particularly, the said PED system uses gantry robotic deposition apparatus equipped with an actuator to control the location of a deposition nozzle to prepare the three-dimensional scaffold. This system enables three-dimensional motion control (x-axis, y-axis, and z-axis) and a syringe is attached on the z-axis motion stage (see FIG. 1). The three-dimensional scaffold was prepared by using this gantry robotic deposition apparatus.

The three-dimensional scaffold prepared above was dried at room temperature for 24 hours, and then dipped in 0.1 M MCPM (Mono Calcium Phosphate Mono Hydrate) solution for 6 hours to induce bone cement reaction. The phase transition of α-TCP was induced into CDHA (Calcium Deficient Hydroxyapatite) by this reaction, leading to hardening. Thereafter, the scaffold was washed with distilled water so that the scaffold was maintained as neutral. The scaffold was dried at room temperature for 48 hours. As a result, the scaffold for hard tissue regeneration containing Quercetein was prepared (see FIG. 1). The characteristics of the prepared hard tissue scaffold and the syringe nozzle used herein were presented below:
1. strut distance of the hard tissue scaffold: 1.0 mm,
2. dimension of the hard tissue scaffold: 10×5×5 mm, and
3. syringe nozzle size: 21 G.

Example 2: Preparation of Scaffold for Hard Tissue Regeneration (Containing 1 μM of Quercetein)

The scaffold for hard tissue regeneration was prepared by the same manner as described in Example 1 except that 1 μM of Quercetein was included in each scaffold instead of 200 μM of Quercetein.

Example 3: Preparation of Scaffold for Hard Tissue Regeneration (Containing 200 μM of Genistein)

The scaffold for hard tissue regeneration was prepared by the same manner as described in Example 1 except that Genistein originated from soybean was used instead of Quercetein originated from onion.

Example 4: Preparation of Scaffold for Hard Tissue Regeneration (Containing 1 µM of Genistein)

The scaffold for hard tissue regeneration was prepared by the same manner as described in Example 2 except that Genistein originated from soybean was used instead of Quercetein originated from onion.

Comparative Example 1: Preparation of Scaffold for Hard Tissue Regeneration (Not Containing Quercetein or Genistein)

The scaffold for hard tissue regeneration that did not contain any active ingredient for bone formation, that is not containing Quercetein or Genistein, was prepared by the same manner as described in Example 1.

Comparative Example 2: Preparation of Scaffold for Hard Tissue Regeneration (Containing 200 µM of Alendronate)

The scaffold for hard tissue regeneration was prepared by the same manner as described in Example 1 except that Alendronate, the conventional osteoporosis treating agent, was used instead of Quercetein originated from onion.

Experimental Example 1: Evaluation of Drug Releasing Characteristics

The following experiment was performed to evaluate the drug releasing characteristics of Quercetein or Genistein included in the scaffold for hard tissue regeneration of the invention.
<1-1> Evaluation of Drug Releasing Characteristics of Quercetein To evaluate the drug releasing characteristics of the active ingredient included in the scaffold, the scaffold for hard tissue regeneration (containing Quercetein by 200 µm/scaffold) prepared in Example 1 was dipped in body fluid like PBS (phosphate buffered saline) or de-ionized water in a 37° C. shaker. Sampling of the solution was performed hourly and the concentration of Quercetein released in the solution was measured. Quercetein is a hydrophobic material, so that it is very difficult to detect the concentration by dissolving. To evaluate the drug releasing activity in a solution where the active material is dissolved, the experiment was equally performed with ethanol, the dissolving solvent. The results are presented in FIG. 2.

Figure 2:
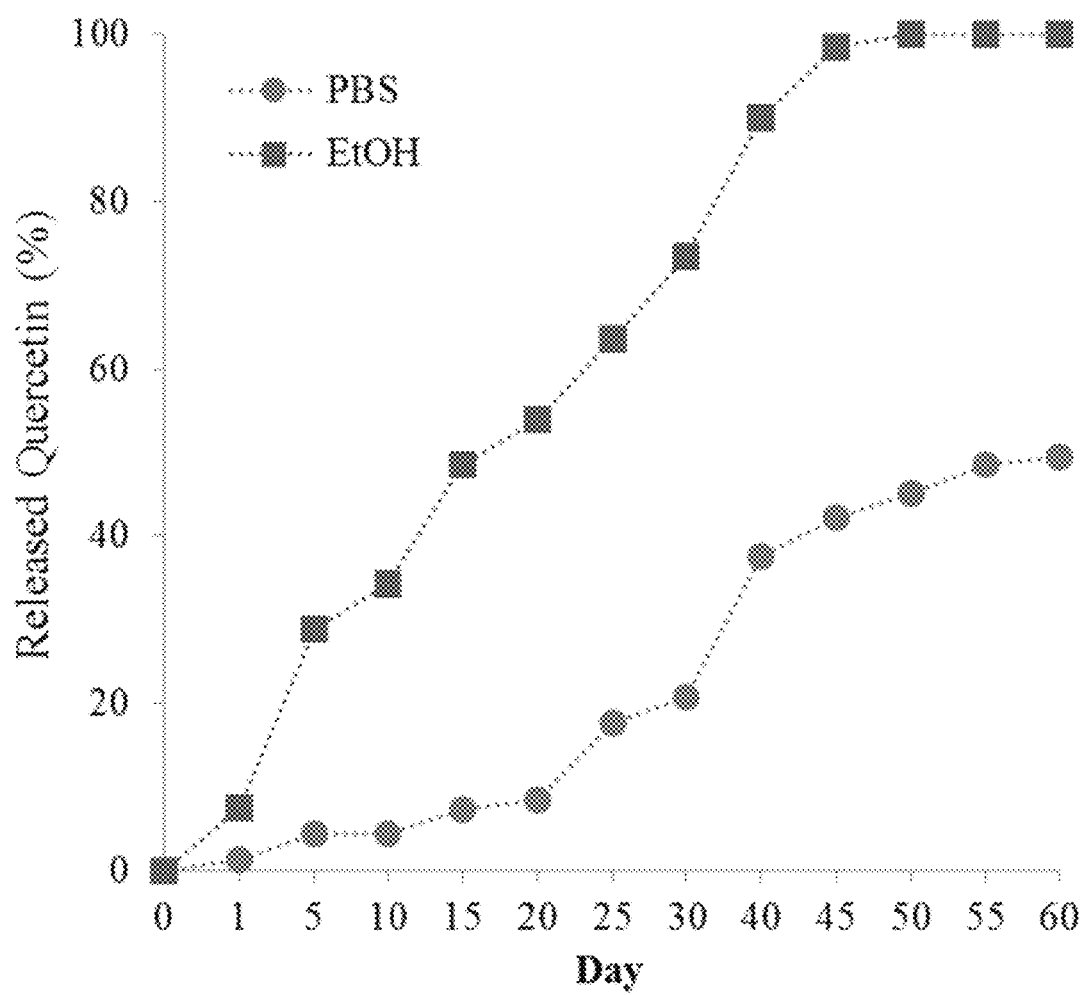
FIG. 2 is a graph illustrating the release characteristics of Quercetein included in the scaffold for hard tissue regeneration prepared in Example 1.

FIG. 2 is a graph illustrating the release characteristics of Quercetein included in the scaffold for hard tissue regeneration prepared in Example 1.

As shown in FIG. 2, Quercetein was 100% sustained-released in ethanol, the dissolving solvent, without early acute release over 40 days of the whole 60 day experimental period, and this release was mainly due to the dissolution. In the meantime, in de-ionized water and PBS, Quercetein was released 10% over the early 20 days and released approximately 50% over 68 days. Quercetein displays a low solubility in an aqueous solution. So, the released amount was mainly the physical release by the biodegradation of the scaffold. That is, the even drug dispersion in the scaffold is an important factor for the continuous active sustained-release of the drug.
<1-2> Evaluation of Drug Releasing Characteristics of Genistein The following experiment was performed by the same manner as described in Example <1-1> except that the scaffold for hard tissue regeneration (containing Genistein by 200 µm/scaffold) prepared in Example 3 instead of the scaffold for hard tissue regeneration (containing Quercetein by 200 µm/scaffold) prepared in Example 1. The results are presented in FIG. 3.

Figure 3:
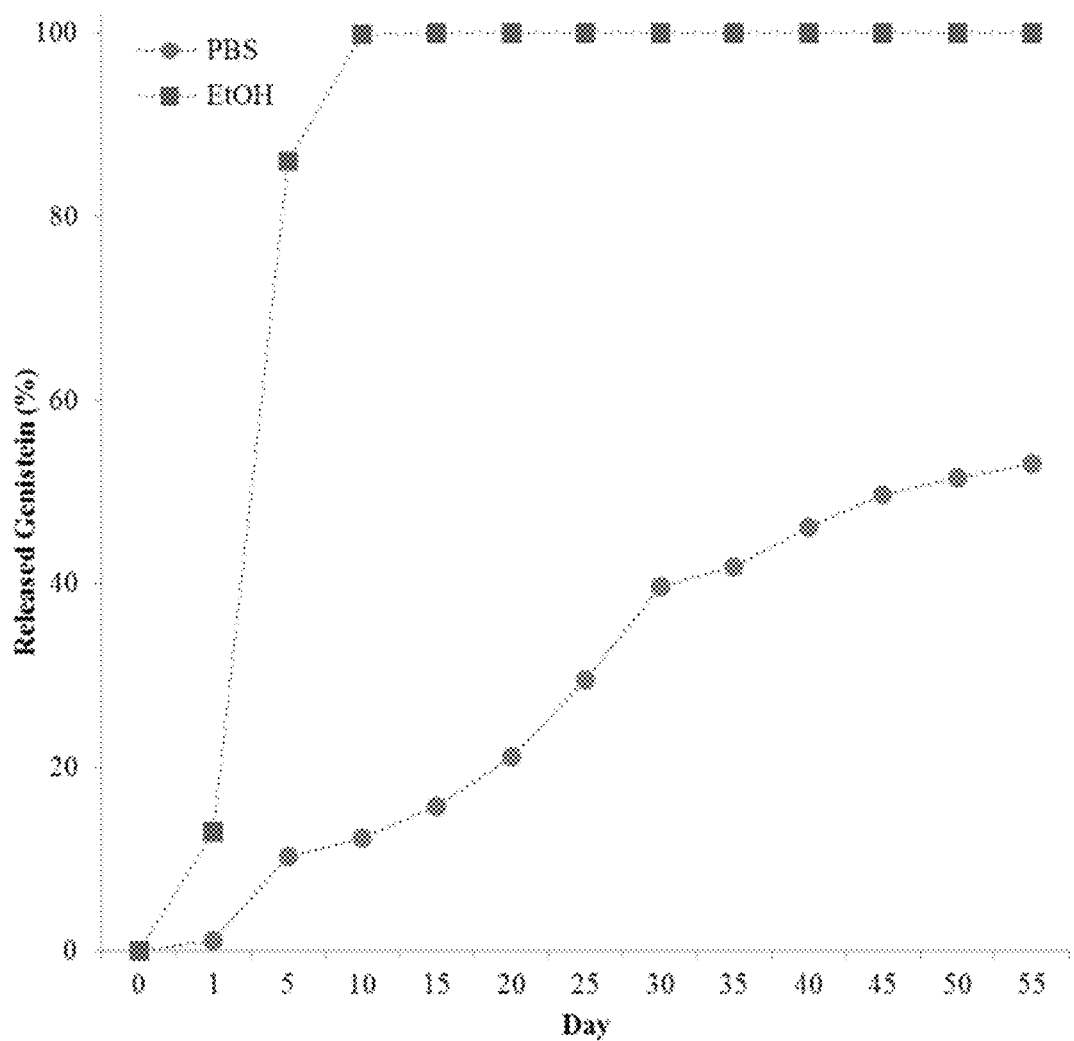
FIG. 3 is a graph illustrating the release characteristics of Genistein included in the scaffold for hard tissue regeneration prepared in Example 2.

FIG. 3 is a graph illustrating the release characteristics of Genistein included in the scaffold for hard tissue regeneration prepared in Example 3.

As shown in FIG. 3, Genistein was released 100% over the early 5 days in ethanol, the dissolving solvent, and this release was mainly due to the dissolution. In particular, compared with the results of Experimental Example <1-1>, the solubility of Genistein was even higher in ethanol, compared with that of Quercetein. Genistein was released 60% over 55 days continuously in de-ionized water and PBS (phosphate buffered saline) without early acute release. Like Quercetein, Genistein also displays a low solubility in an aqueous solution. So, the released amount was mainly the physical release by the biodegradation of the scaffold. That is, the even drug dispersion in the scaffold is an important factor for the continuous active sustained-release of the drug.

Experimental Example 2: Evaluation of Osteoblast Proliferation Activity

To investigate the changes of the osteoblast proliferation activity according to the concentration of the drug, the following experiment was performed.
<2-1> Observation of Osteoblast Activity According to the Concentration of Quercetein MC3T3-E1 cells (MC3T3-E1 Subclone 4, ATCC CRL-2593, obtained from ATCC) were cultured in α-MEM (α-Minimum Essential Medium, GIBCO) supplemented with FBS (Fetal Bovine Serum) and penicillin/streptomycin under the standard culture condition (37° C., 5% $CO_2$). When the cells were grown to 70~80% confluency, the cells were trypsinized. Then, the cells were collected by centrifugation.

The collected MC3T3-E1 cells were seeded at the density of $1.0 \times 10^4$ cells, followed by standard culture for 2 hours. The medium containing Quercetein at the concentrations of 0, 1, 10, 50, 100, and 200 µm was added thereto.

To observe the metabolic activity of the seeded MC3T3-E1 cells, colorimetric 3-(4,5-dimethylthiazole-2-yl)-5-(3-carboxymethoxyphenol)-2-(4-sulfophenyl)-2H-tetrazolium (MTS) assay (CellTiter 96® AQeous One solution Cell Proliferation Assay, Promega) was performed according to the manufacturer's instruction. The MTS tetrazolium compound is converted biologically and dissolved in the tissue culture medium by the cells into a formazan product displaying highest absorbance at 490 nm. The changes of osteoblast proliferation activity were observed on day 1, day 3, and day 5 and the results are shown in FIG. 4.

Figure 4:
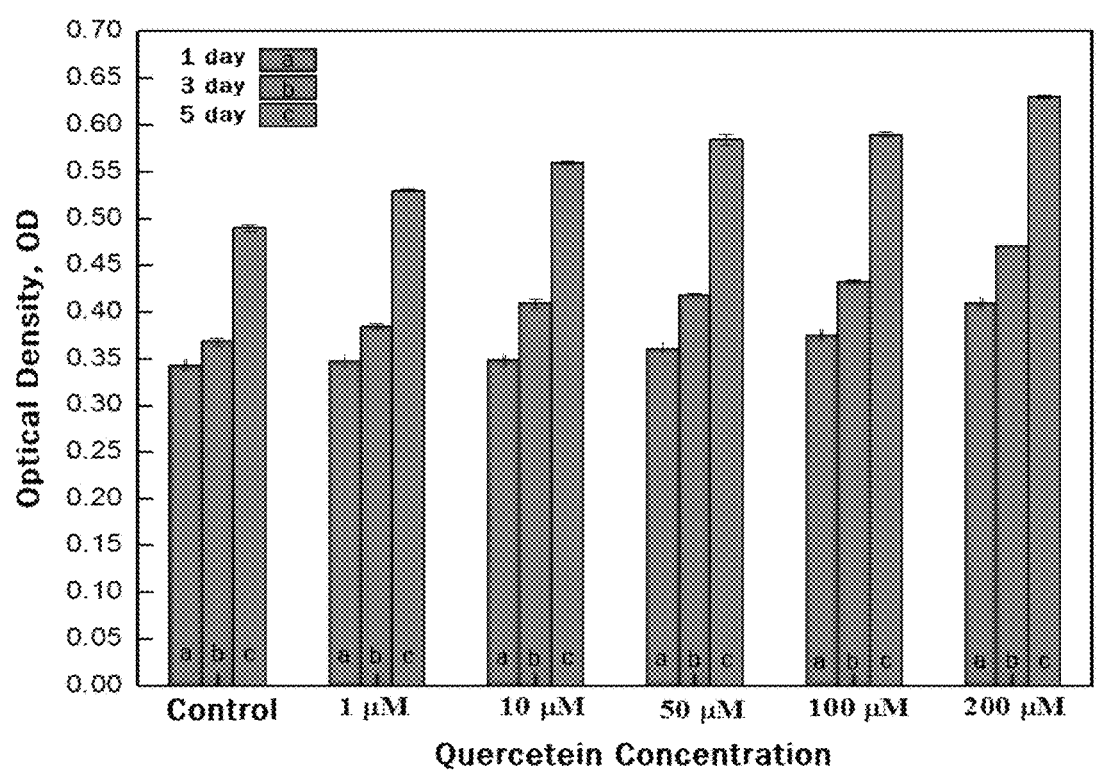
FIG. 4 is a graph illustrating the changes of osteoblast proliferation activity according to the concentration of Quercetein.

FIG. 4 is a graph illustrating the changes of osteoblast proliferation activity according to the concentration of Quercetein.

As shown in FIG. 4, compared with the cells not treated with Quercetein (non-treated group), the proliferation of osteoblasts was increased Quercetein dose-dependently. Particularly, as the concentration of Quercetein was increased from 1 to 200 µM, the proliferation of osteoblasts was increased Quercetein dose-dependently. Therefore, the preferable concentration of Quercetein was determined to be 1~200 µM.

<2-2> Observation of Osteoblast Activity According to the Concentration of Genistein The following experiment was performed by the same manner as described in Experimental Example <2-1> except that Genistein was used instead of Quercetein. The results are presented in FIG. 5.

Figure 5:
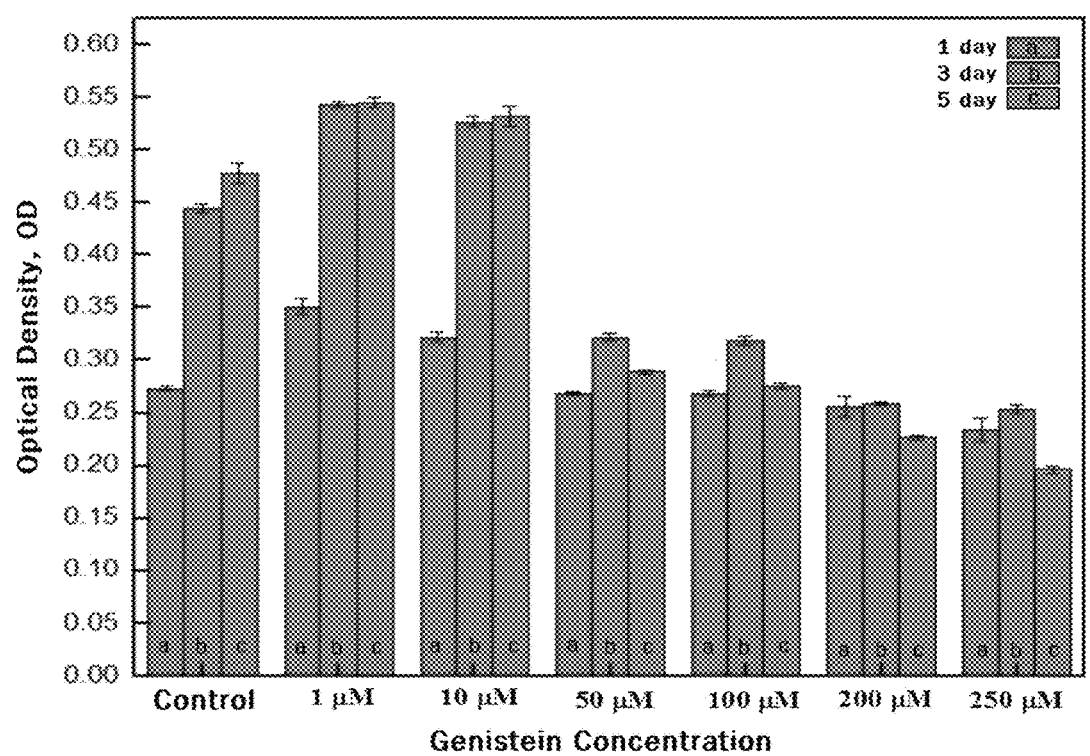
FIG. 5 is a graph illustrating the changes of osteoblast proliferation activity according to the concentration of Genistein.

FIG. 5 is a graph illustrating the changes of osteoblast proliferation activity according to the concentration of Genistein.

As shown in FIG. 5, compared with the cells not-treated with Quercetein (non-treated group), as the concentration of Genistein was increased from 1 to 10 μM, the proliferation of osteoblasts was increased. If the concentration of Genistein was increased over 10 μM, the proliferation of osteoblasts was rather inhibited. So, the preferable concentration of Genistein was determined to be 1~10 μM. The proliferation of osteoblasts at the concentration range 1~10 μM was not much changed, so the most preferable concentration of Genistein would be 1 μM.

<2-3> Observation of Osteoblast Activity According to the Concentration of Alendronate To compare the effects of the conventional osteoporosis treating agent Alendronate, and the polyphenol-based natural substance Quercetein or Genistein, Alendronate was added to osteoblasts at the same concentration as those of Quercetein and Genistein as shown in Experimental Examples <2-1> and <2-2>, followed by observation of the proliferation of osteoblasts. The experiment was performed by the same manner as described in Experimental Examples <2-1> and <2-2> except that Alendronate was used instead of Quercetein or Genistein and at this time the concentration of Alendronate was 1 μM or 200 μM. The results are presented in FIG. 6.

Figure 6:
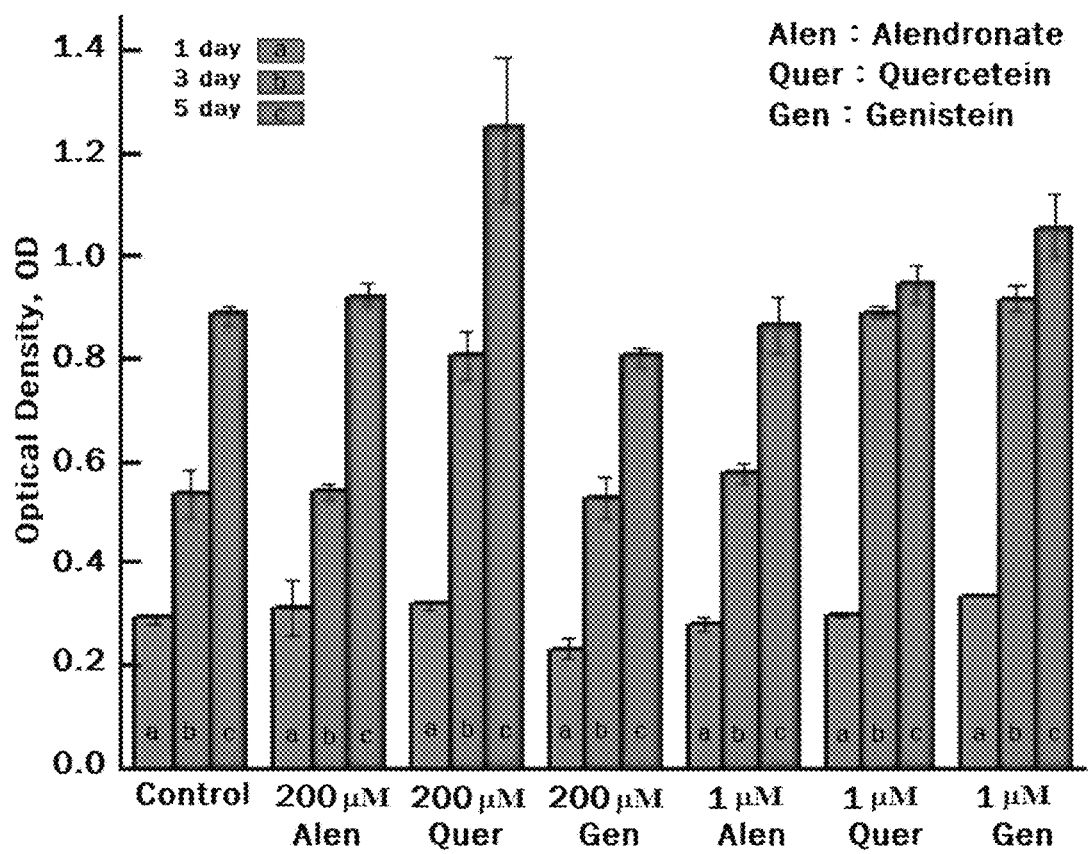
FIG. 6 is a graph illustrating the changes of osteoblast proliferation activity according to the administration of Quercetein, Genistein, and Alendronate at the same dose.

FIG. 6 is a graph illustrating the changes of osteoblast proliferation activity according to the administration of Quercetein, Genistein, and Alendronate at the same dose.

As shown in FIG. 6, Quercetein and Genistein had the similar or a little better effect on osteoblasts than Alendronate. Particularly, at the concentration of 200 μM, Genistein and Alendronate displayed the similar effect on the proliferation of osteoblasts, but Quercetein increased the proliferation significantly, compared with Alendronate, observed on day 3 and day 5. At the concentration of 1 μM, both Quercetein and Genistein promoted the proliferation of osteoblasts, observed on day 3 and day 5, and at this time the promoting effect of Genistein was greater than that of Quercetein. That is, the natural substances Quercetein and Genistein had similar or more excellent effect of promoting the osteoblast differentiation than the conventional drug Alendronate.

<2-4> Observation of the Effect of the Scaffold for Hard Tissue Regeneration Containing Quercetein and Genistein The scaffolds for hard tissue regeneration prepared in Examples 1~4 and Comparative Example 1 were sterilized by dipping in 70% ethanol for 1 hour under UV irradiation, which were then washed three times with PBS (Phosphate Buffered Saline). To prevent contamination or pH change during the cell culture, the scaffolds were dipped in cell culture media without MC3T3-E1 cells for a day under the standard culture conditions.

Thereafter, MC3T3-E1 cells were seeded in the scaffolds for hard tissue regeneration prepared in Example 1~4 and Comparative Example 1 at the density of $1.0 \times 10^5$ cells/scaffold, followed by standard culture for 2 hours. Then, the media were added thereto. To eliminate the non-attached cells in the course of the experiment, the media were regularly replaced. The proliferation of osteoblasts was observed on day 1, day 3, and day 5. The results are shown in FIG. 7.

Figure 7:
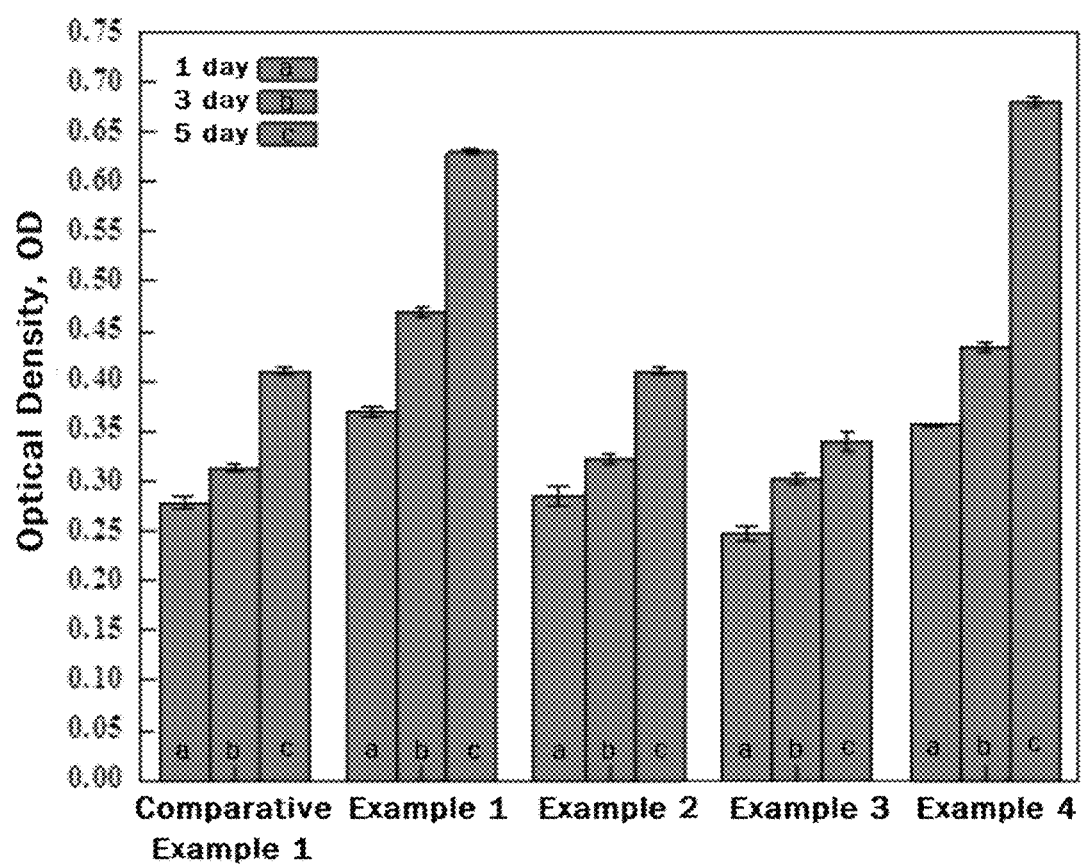
FIG. 7 is a graph illustrating the changes of osteoblast proliferation activity according to the different concentrations of Quercetein and Genistein included in the scaffold for hard tissue regeneration of the invention.

FIG. 7 is a graph illustrating the changes of osteoblast proliferation activity according to the different concentrations of Quercetein and Genistein included in the scaffold for hard tissue regeneration of the invention.

As shown in FIG. 7, the proliferation of osteoblasts was significantly promoted by the scaffolds for hard tissue regeneration prepared in Example 1 (200 μM Quercetein/scaffold) and Example 4 (1 μM Genistein/scaffold), compared with the scaffold for hard tissue regeneration prepared in Comparative Example 1 (non-treated).

Experimental Example 3: Evaluation of Osteoclast Proliferation Activity

To observe the changes of osteoclast proliferation activity according to the concentration of the active ingredient included in the scaffold for hard tissue regeneration of the invention, the following experiments were performed.

Figure 8:
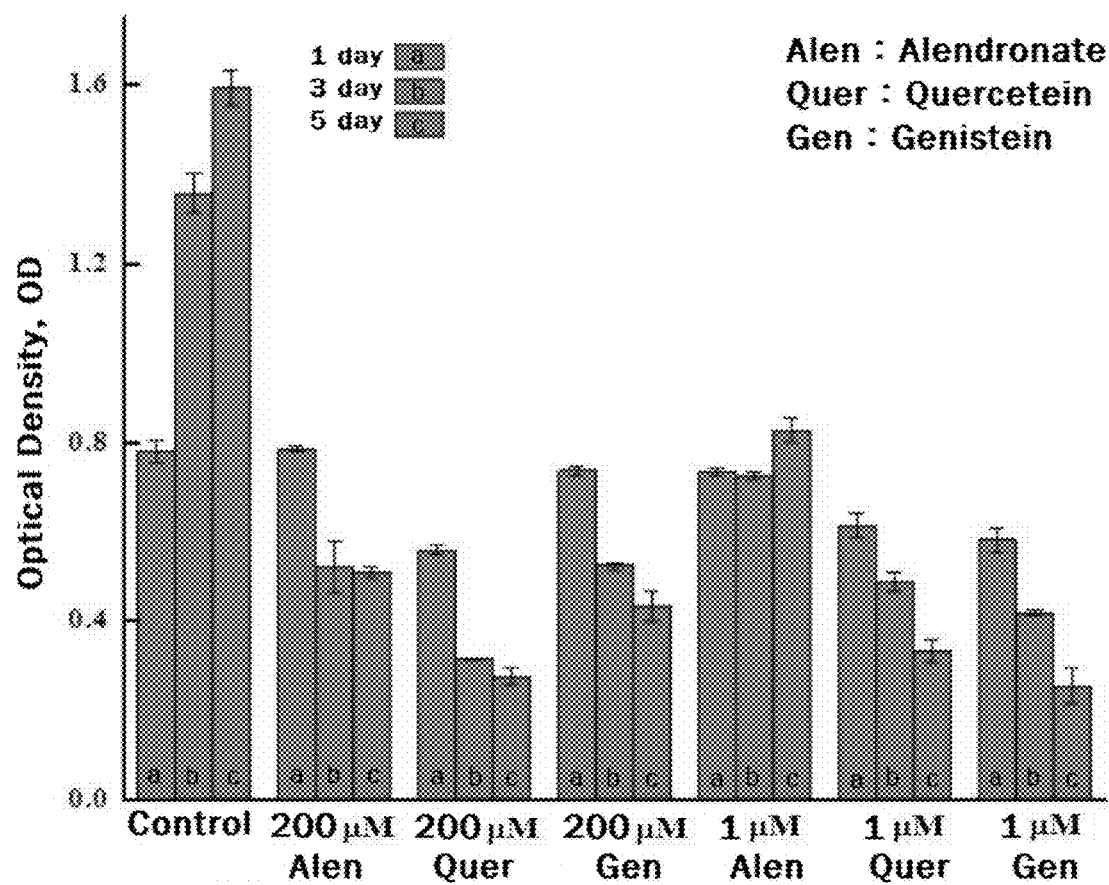
FIG. 8 is a graph illustrating the changes of osteoclast proliferation activity according to the administration of Quercetein, Genistein, and Alendronate at the same dose.

<3-1> Observation of the Effects of the Natural Substance (Quercetein or Genistein) and Alendronate on the Proliferation of Osteoclasts The experiment was performed by the same manner as described in Experimental Example <2-3> except that RAW 264.7 cells, the multinuclear osteoclasts treated with RANKL (Receptor Activation for Nuclear Factor κB Ligand), were used instead of MC3T3-E1 cells (MC3T3-E1 Subclone 4, ATCC CRL-2593, obtained from ATCC), and the results are presented in FIG. 8.

FIG. 8 is a graph illustrating the changes of osteoclast proliferation activity according to the administration of Quercetein, Genistein, and Alendronate at the same dose.

As shown in FIG. 8, the proliferation of osteoclasts was significantly inhibited by Quercetein, Genistein, or Alendronate, compared with the case not treated with those drugs. In particular, when treated with those drugs at the same dose, Quercetein was most excellent in inhibiting the proliferation of osteoclasts at the concentration of 200 μM, while the Genistein was most excellent in inhibiting the proliferation of osteoclasts at the concentration of 1 μM. That is, the natural substance (Quercetein or Genistein) had the similar or greater inhibitory effect on the proliferation of osteoclasts than Alendronate.

Figure 9:
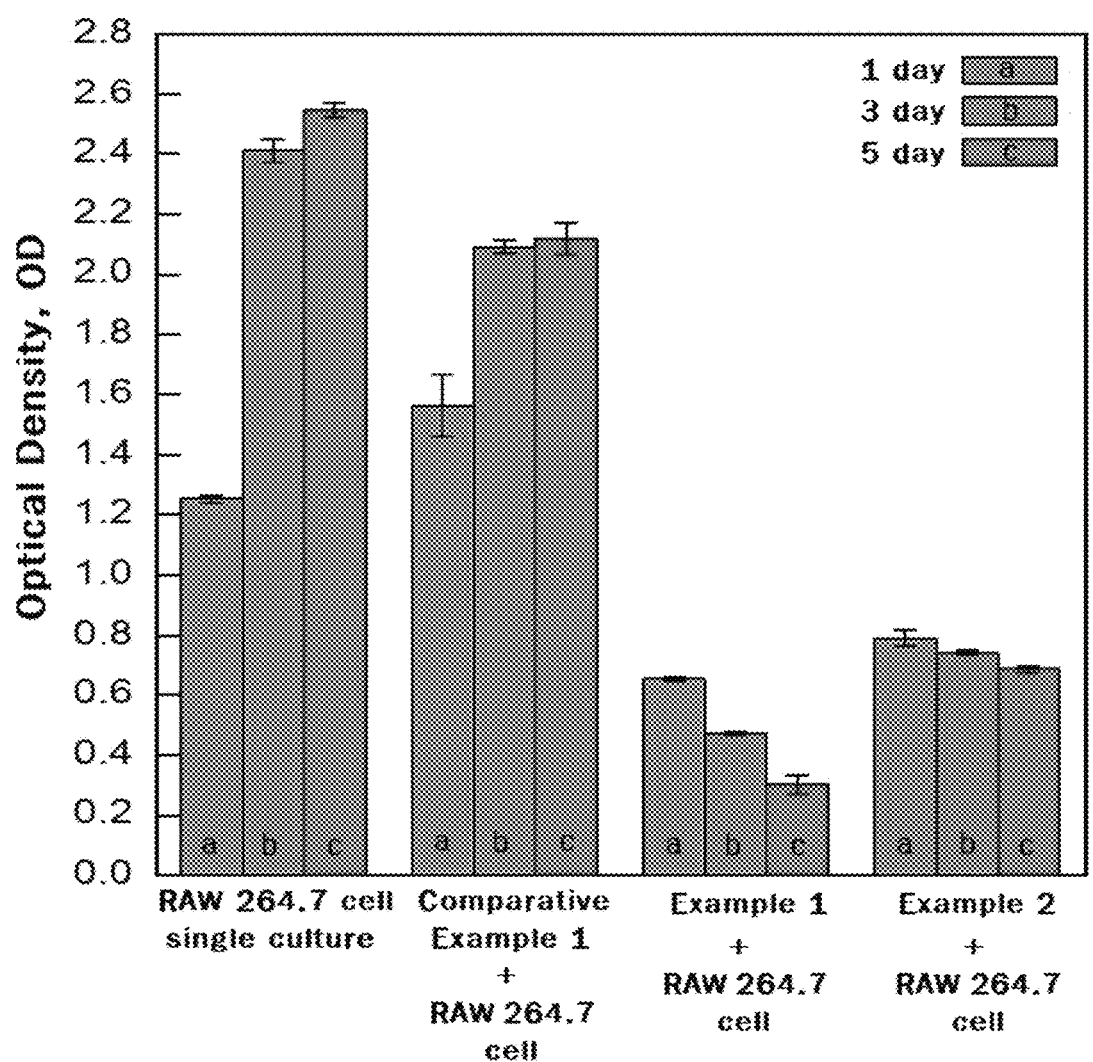
FIG. 9 is a graph illustrating the changes of osteoclast proliferation activity according to the concentration of Quercetein included in the scaffold for hard tissue regeneration of the invention.

<3-2> Observation of the Effect of the Scaffold for Hard Tissue Regeneration Containing Quercetein The experiment was performed by the same manner as described in Experimental Example <2-4> except that RAW 264.7 cells prepared in Experimental Example <3-1> were used instead of MC3T3-E1 cells, and the results are presented in FIG. 9.

FIG. 9 is a graph illustrating the changes of osteoclast proliferation activity according to the concentration of Quercetein included in the scaffold for hard tissue regeneration of the invention.

As shown in FIG. 9, the scaffold for hard tissue regeneration containing 1 μM or 200 μM of Quercetein was more efficient in inhibiting the proliferation of osteoclasts than the scaffold for hard tissue regeneration not containing Quercetein. In particular, the highest inhibitory effect was observed at the concentration of 200 μM.

Figure 10:
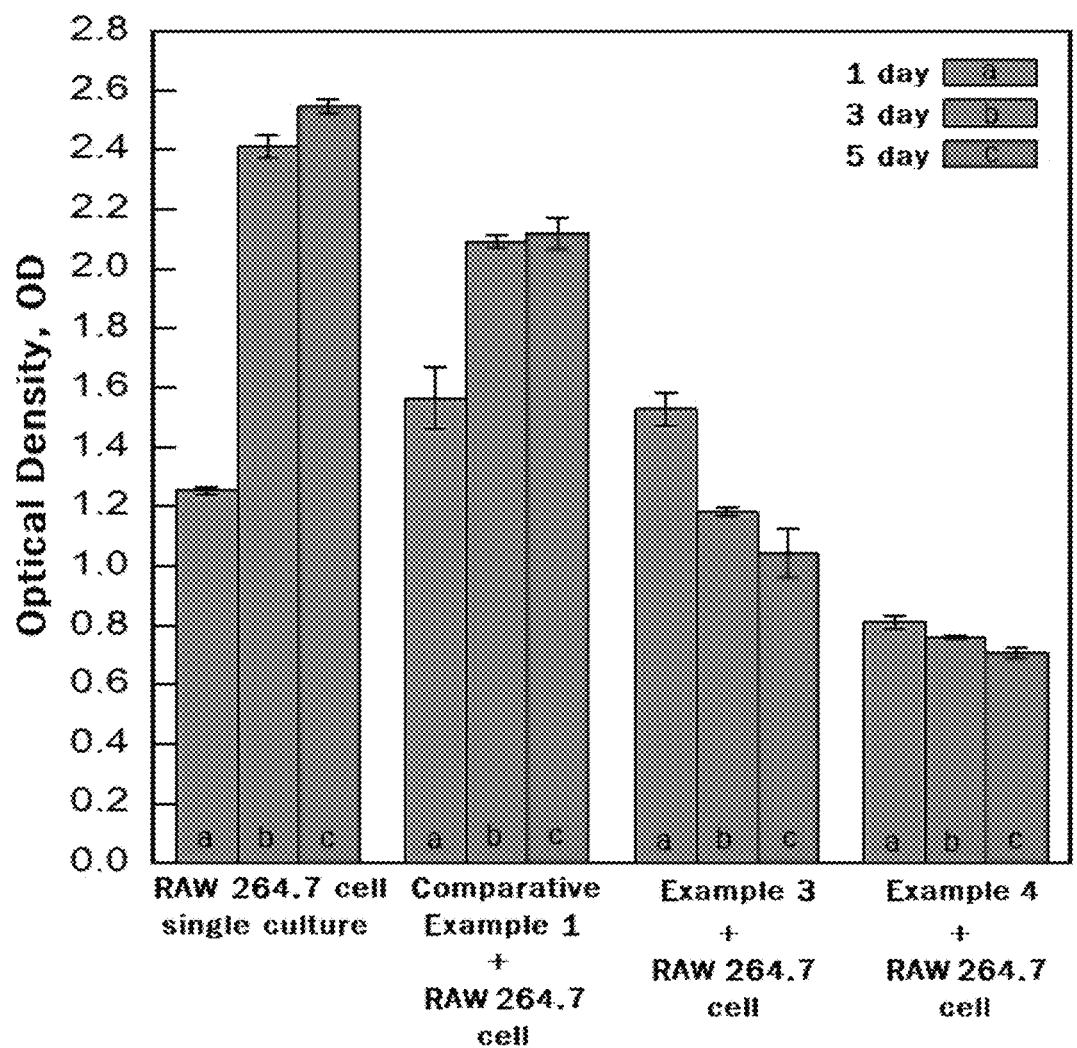
FIG. 10 is a graph illustrating the changes of osteoclast proliferation activity according to the concentration of Genistein included in the scaffold for hard tissue regeneration of the invention.

<3-3> Observation of the Effect of the Scaffold for Hard Tissue Regeneration Containing Genistein The experiment was performed by the same manner as described in Experimental Example <3-2> except that the scaffold for hard tissue regeneration containing Genistein was used instead of the scaffold for hard tissue regeneration containing Quercetein, and the results are presented in FIG. 10.

FIG. 10 is a graph illustrating the changes of osteoclast proliferation activity according to the concentration of Genistein included in the scaffold for hard tissue regeneration of the invention.

As shown in FIG. 10, the scaffold for hard tissue regeneration containing 1 μM or 200 μM of Genistein was more efficient in inhibiting the proliferation of osteoclasts than the scaffold for hard tissue regeneration not containing Genistein. In particular, the highest inhibitory effect was observed at the concentration of 1 μM.

Experimental Example 4: Evaluation of the Early Differentiation of Osteoblasts

The early differentiation of osteoblasts can be evaluated by investigating the activity of alkaline phosphatase, for which the following experiment was performed by using QuantiChrom™ Alkaline Phosphatase Assay Kit (DALP-250, BioAssay Systems).

MC3T3-E1 cells were seeded by the same manner as described in Experimental Example <2-4> except that ascorbic acid was added to the medium to induce the differentiation of osteoblasts. The medium of the well plate on the culture was well mixed and 50 μl of nPP ((p-Nitrophenyl) phosphate) solution was added to each well containing 100 μl of the medium, followed by culture for 60 minutes. 100 μl of the color-developed solution was loaded in each well of a 96-well plate, and $OD_{450}$ was measured. All the medium was discarded and the plate was washed with PBS, to which ALP-kit assay buffer was added (500 μl/well), followed by reaction for 10 minutes. The buffer was well mixed by stirring tens of times strongly with a pipette. The solution was collected and centrifuged at 13,000 rpm for 3 minutes. The supernatant was transferred in a well plate (100 μl/well), to which nPP solution was added (50 μl/well), followed by culture for 60 minutes. 100 μl of the color-developed solution was loaded in each well of a 96-well plate, and $OD_{450}$ was measured. Absorbance of the medium and extracellular absorbance were measured and combined for the calculation with the following formula.

ALP activity=absorbance/measured amount/time

Standardized ALP activity=ALP activity/cell number

The measurement of alkaline phosphatase activity means to measure the activity of a specific enzyme that is involved in dephosphorylation of a specific substrate. Alkaline phosphatase is an important factor for bone generation and the activity thereof is increased as the osteoblast activity increases. So, the differentiation of MC3T3-E1 cells into osteoblasts can be evaluated through the above experiment. The results are presented in FIG. 11.

Figure 11:
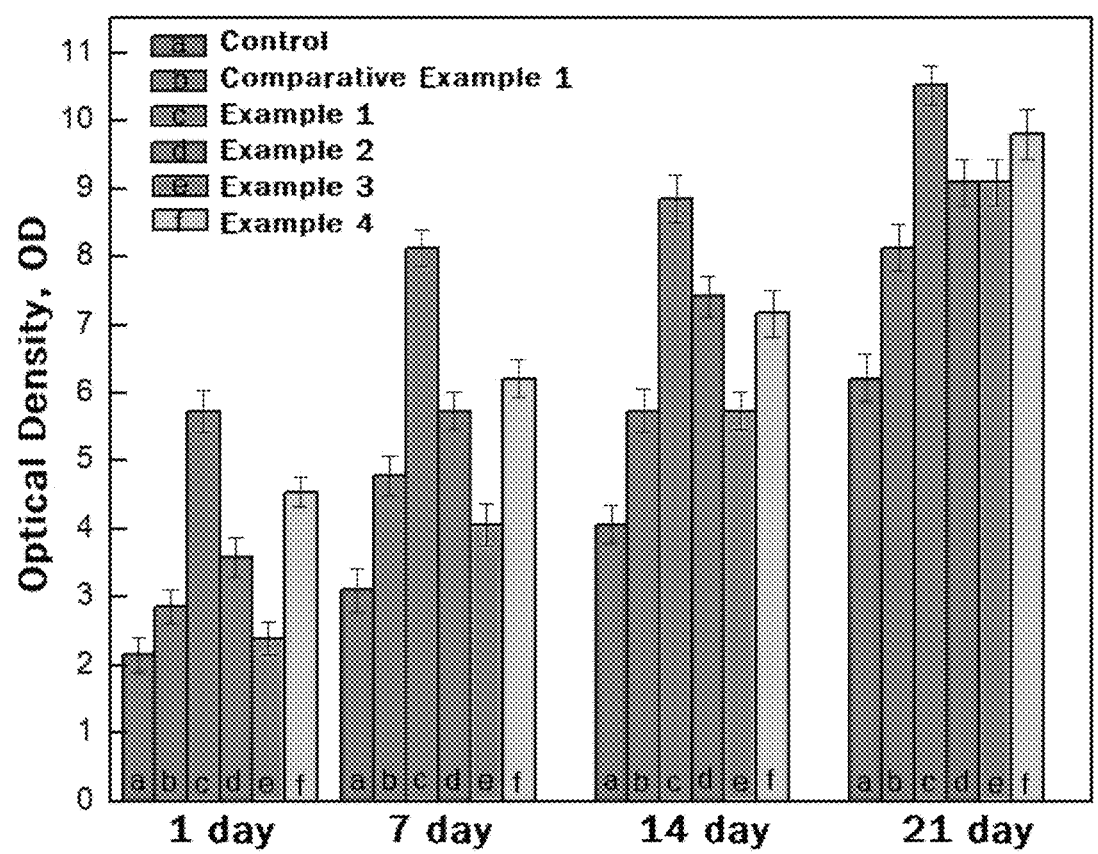
FIG. 11 is a graph illustrating the effect of the scaffold for hard tissue regeneration containing Quercetein or Genistein on the early differentiation of osteoblasts, observed by tracing the changes of alkaline phosphatase activity.

FIG. 11 is a graph illustrating the effect of the scaffold for hard tissue regeneration containing Quercetein or Genistein on the early differentiation of osteoblasts, observed by tracing the changes of alkaline phosphatase activity.

As shown in FIG. 11, the scaffold for hard tissue regeneration containing Quercetein or Genistein induced the activation of alkaline phosphatase, so that it promoted the early differentiation of osteoblasts. In particular, the scaffold containing 200 μM of Quercetein (Example 1) and the scaffold containing 1 μM of Genistein (Example 4) were confirmed to have excellent promoting effect on the early osteogenic differentiation.

That is, it was confirmed that the scaffold containing the natural substance Quercetein or Genistein at a certain concentration had the effect of accelerating the early osteogenic differentiation of osteoblasts.

Experimental Example 5: Evaluation of Osteogenic Differentiation of Osteoblasts by Real-Time PCR (Polymerase Chain Reaction)

To observe the effect of Quercetein or Genistein included in the scaffold for hard tissue regeneration of the present invention on osteogenic differentiation of osteoblasts, real-time PCR was performed to examine the activity of such factors involved in the early or late osteogenic differentiation of osteoblasts as collagen type-I (Col-I), Runx2, alkaline phosphatase (ALP), osteocalcin (OC), or bone sialoprotein (BSP).

MC3T3-E1 cells (MC3T3-E1 Subclone 4, ATCC CRL-2593, obtained from ATCC) were seeded in the scaffolds for hard tissue regeneration prepared in Example 1, Example 4, and Comparative Example 1, at the density of $1.0 \times 10^5$ cells/scaffold. 24 hours later, the culture medium (α-MEM (α-Minimum Essential Medium, GIBCO) supplemented with 10% FBS (Fetal Bovine Serum), 100 μg/ml penicillin, and 100 μg/ml streptomycin) was replaced with osteogenic culture medium supplemented with 10 mM β-glycerophosphate and 50 μg/ml L-ascorbate-2 phosphate (Sigma). The cells were collected on day 7, day 14, day 21, and day 28. Total RNA was extracted by using illustra RNA spin Mini RNA isolation Kit (GE Healthcare) according to the manufacturer's instruction. Then, cDNA was synthesized by using Superscript II (Invitrogen). PCR was performed with the osteogenic marker primers (collagen type-I (Col-I), Runx2, alkaline phosphatase (ALP), osteocalcin (OC), and bone sialoprotein (BSP)), by using ABI 7500 real-time PCR machine (Applied Biosystem). Each sample was triplicated and standardized by GAPDH (glyceraldehyde 3-phosphate dehydrogenase). The results of each osteogenic marker primer on the scaffolds prepared in Example 1, Example 4, and Comparative Example 1 were compared and the relative values were presented in FIGS. 12~16.

Figure 12:
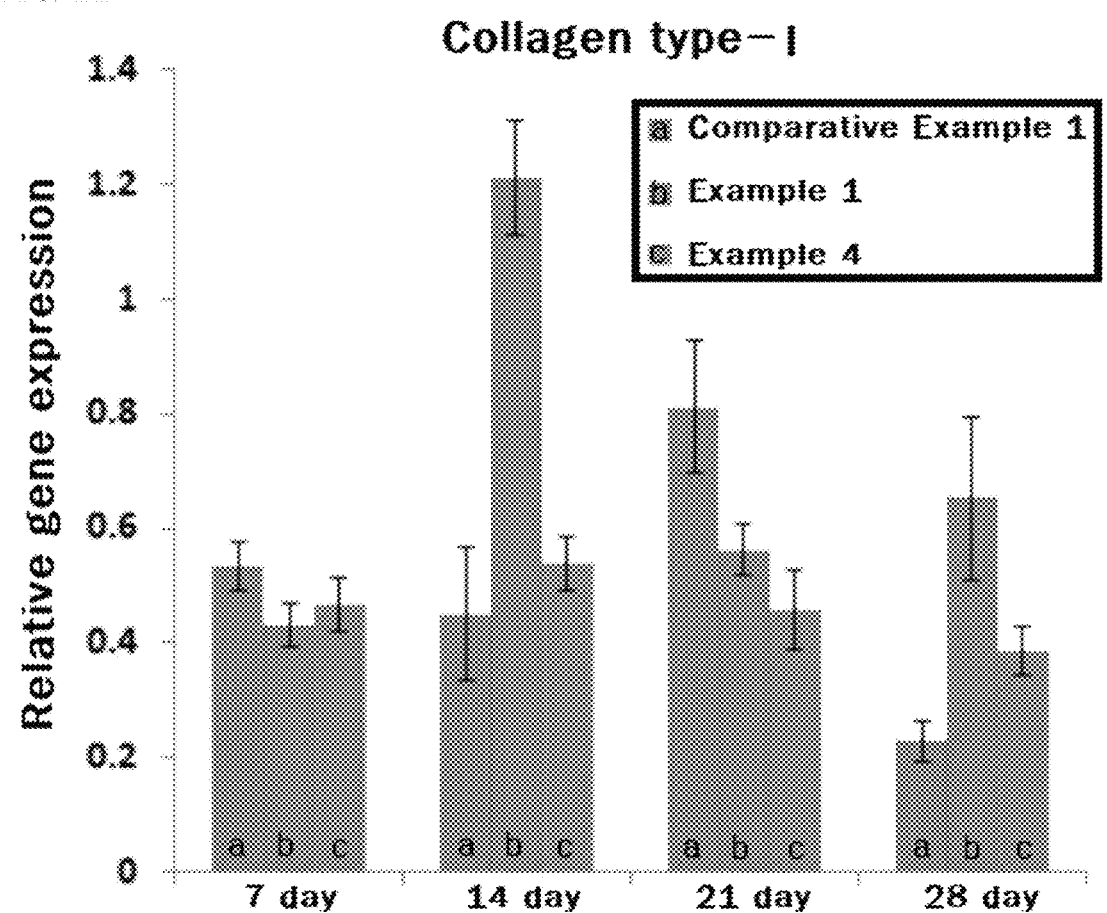
FIG. 12 is a graph illustrating the relative gene expression of collagen type-1 (Col-I), one of the osteogenic marker primers.

FIG. 12 is a graph illustrating the relative gene expression of Runx2, one of the osteogenic marker primers.

Figure 13:
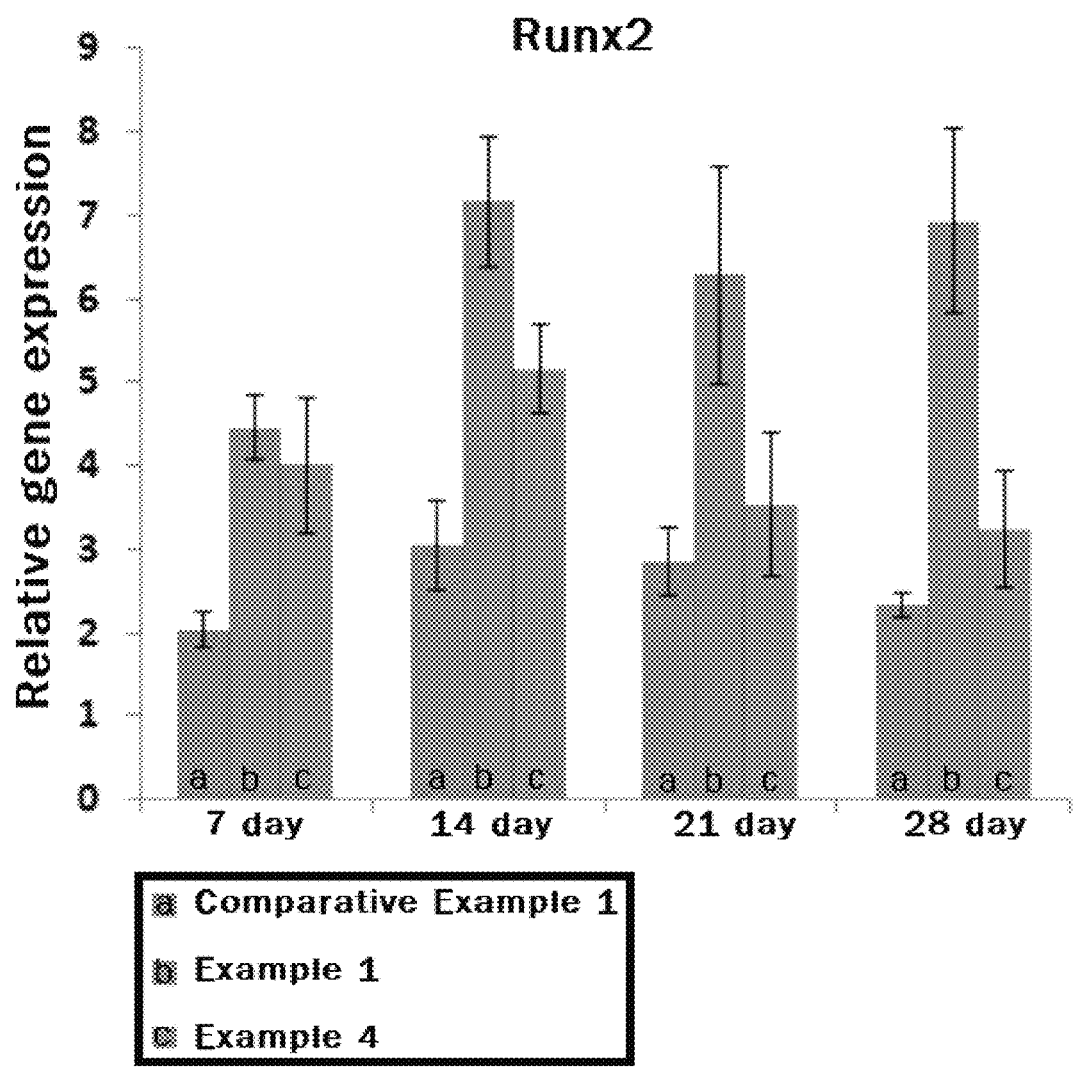
FIG. 13 is a graph illustrating the relative gene expression of Runx2, one of the osteogenic marker primers.

FIG. 13 is a graph illustrating the relative gene expression of collagen type-1 (Col-I), one of the osteogenic marker primers.

Figure 14:
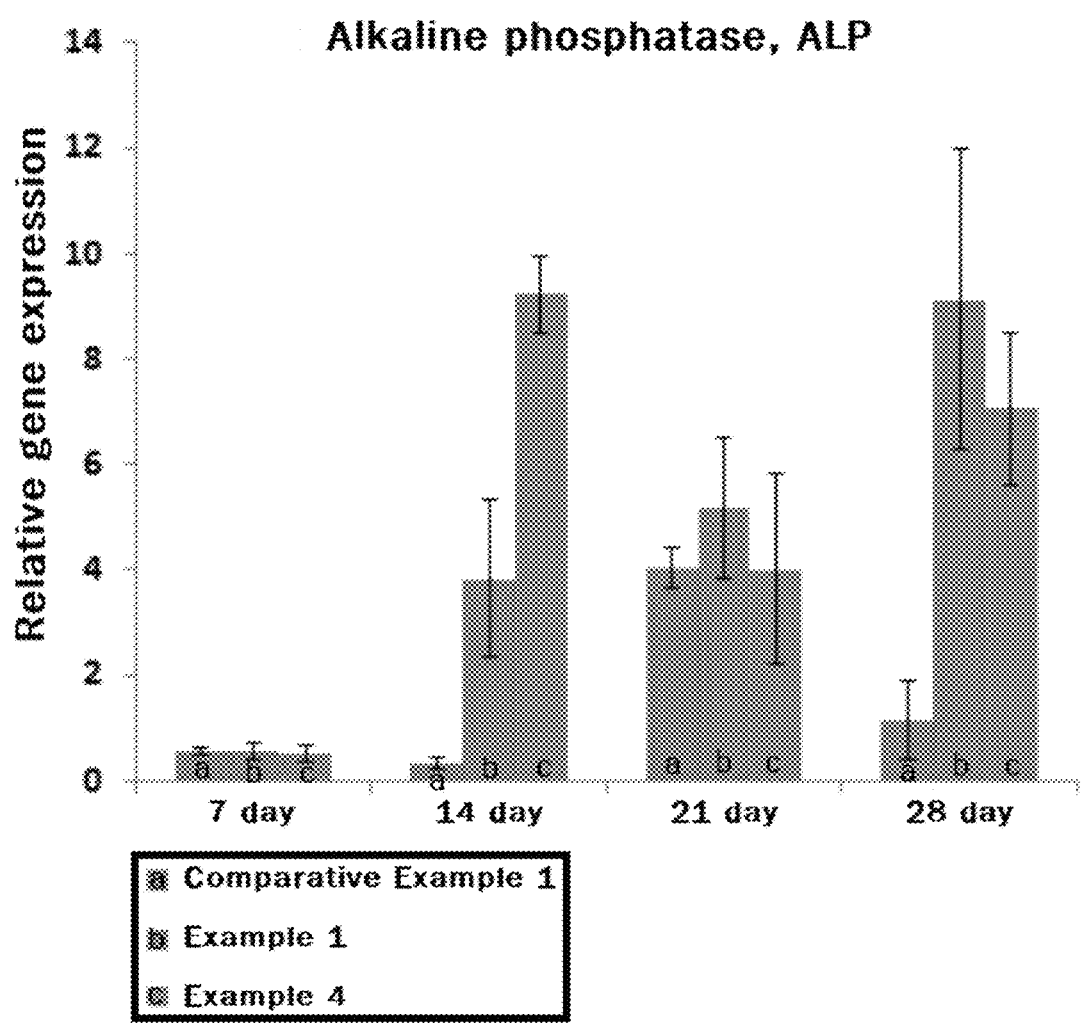
FIG. 14 is a graph illustrating the relative gene expression of alkaline phosphatase (ALP), one of the osteogenic marker primers.

FIG. 14 is a graph illustrating the relative gene expression of alkaline phosphatase (ALP), one of the osteogenic marker primers.

Figure 15:
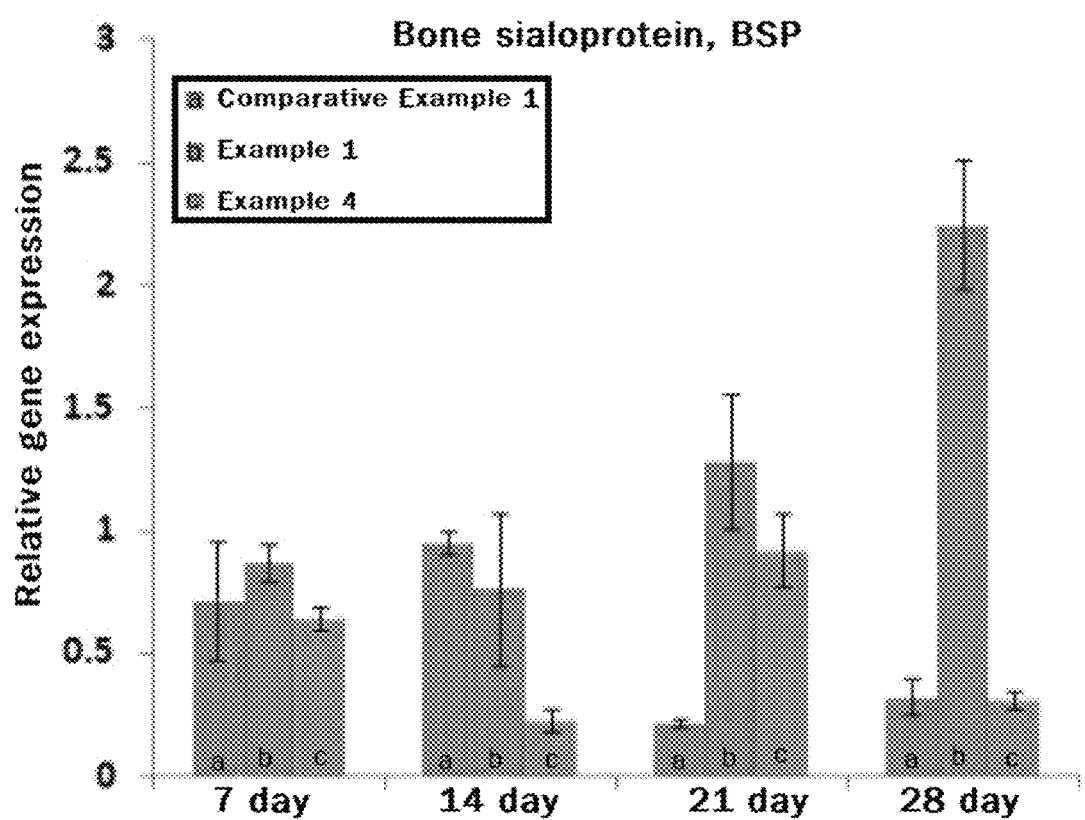
FIG. 15 is a graph illustrating the relative gene expression of bone sialoprotein (BSP)), one of the osteogenic marker primers.

FIG. 15 is a graph illustrating the relative gene expression of bone sialoprotein (BSP)), one of the osteogenic marker primers.

Figure 16:
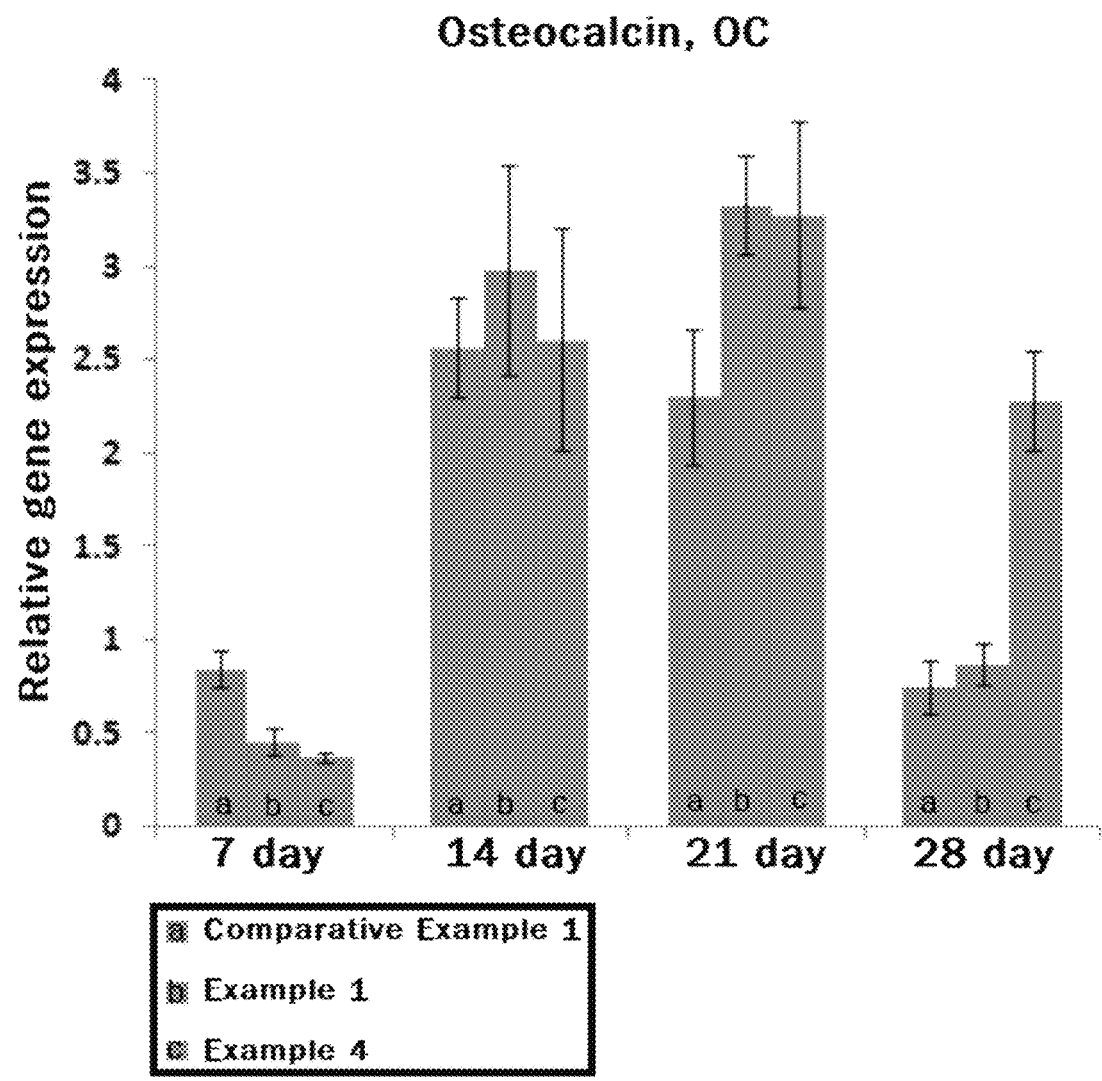
FIG. 16 is a graph illustrating the relative gene expression of osteocalcin (OC), one of the osteogenic marker primers.

FIG. 16 is a graph illustrating the relative gene expression of osteocalcin (OC), one of the osteogenic marker primers.

As shown in FIGS. 12~16, when osteoblasts were seeded in the scaffolds for hard tissue regeneration prepared in Example 1 and Example 4, the osteogenic activity of osteoblasts was accelerated over the time, compared with when osteoblasts were seeded in the scaffold for hard tissue regeneration prepared in Comparative Example 1. More particularly, the expression of collagen type I (Col-I) was significantly induced in the scaffold prepared in Example 1 from day 14, compared with that in the scaffold prepared in Comparative Example 1.

The expression of Runx2 was also highly promoted in the scaffolds prepared in Example 1 and Example 4 from day 7, compared with that in the scaffold prepared in Comparative Example 1.

The expression of alkaline phosphatase was also highly promoted from day 14 in the scaffolds prepared in Example 1 and Example 4, compared with the scaffold prepared in Comparative Example 1, and osteocalcin was significantly up-regulated from day 21 in the scaffolds prepared in Example 1 and Example 4.

The expression of bond sialoprotein (BSP) was also significantly increased in the scaffolds prepared in Example 1 and Example 4, compared with the scaffold prepared in Comparative Example 1.

That is, the scaffold containing the polyphenol-based natural substance Quercetein or Genistein at a certain concentration accelerated the osteogenic differentiation of osteoblasts.

Experimental Example 6: Observation of the Effect of Drug Release on Bone Mineralization To investigate the effect of the release of Quercetein or Genistein included in the scaffold for hard tissue regeneration of the present invention on bone mineralization, the following experiment was performed.

First, the scaffolds for hard tissue regeneration prepared in Examples 1 and 2 and Comparative Example 1 were dipped in 70% ethanol for 1 hour under UV irradiation, and then they were washed with PBS. To prevent contamination or pH change during the cell culture, the scaffolds were dipped in cell culture medium ($\alpha$-MEM ($\alpha$-Minimum Essential Medium, GIBCO) supplemented with FBS (Fetal Bovine Serum), penicillin (Keunhwa pharmaceutical), and streptomycin (Donga pharmaceutical)) without cells for a day under the standard culture condition (37° C., 5% $CO_2$). Then, MC3T3-E1 cells were cultured in $\alpha$-MEM ($\alpha$-Minimum Essential Medium, GIBCO) supplemented with FBS (Fetal Bovine Serum) and penicillin/streptomycin When the cells were grown to 70~80%, the cells were trypsinized. Then, MC3T3-E1 cells (MC3T3-E1 Subclone 4, ATCC CRL-2593, obtained from ATCC) were selected as osteoblasts, which were cultured in the medium containing the scaffold for hard tissue regeneration prepared in Example 1, Example 2, or Comparative Example 1 under the standard culture condition (37° C., 5% $CO_2$) until cell confluency reached 80%.

14 days later, the scaffold for hard tissue regeneration was washed with PBS, which was then fixed in 10% (v/v) formaldehyde (Sigma-Aldrich) at room temperature for 15 minutes. The scaffold was washed with excessive water and alizarin red S (pH 4.1) was added thereto (1 mL/well). The plate was shaken for 20 minutes at room temperature. Unstained dye was absorbed and the plate was washed again with 4 mL of water four times with shaking. To remove excessive water, the plate was canted for 2 minutes. After re-absorption, the plate was stored at −20° C. before extracting dye. Then, the degree of dyeing was confirmed by phase microscopy. The results are presented in FIG. 17.

Figure 17A:
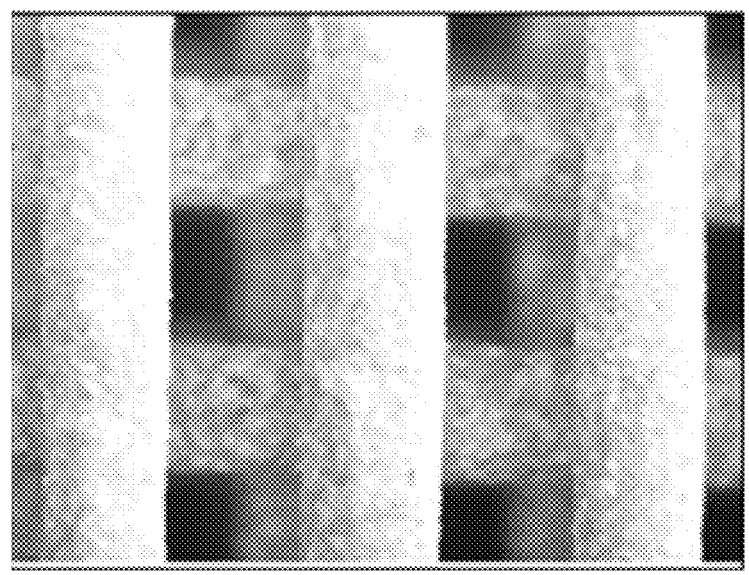
FIG. 17(A) is an image illustrating the scaffold for hard tissue regeneration prepared in Comparative Example 1 stained with alizarin red S without cell culture.

FIG. 17(A) is an image illustrating the scaffold for hard tissue regeneration prepared in Comparative Example 1 stained with alizarin red S without cell culture.

Figure 17B:
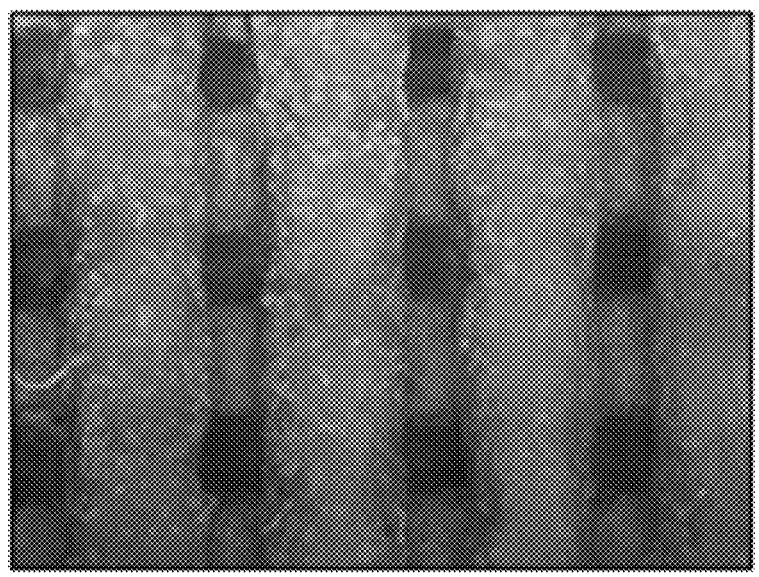
FIG. 17(B) is an image illustrating the scaffold for hard tissue regeneration prepared in Comparative Example 1 stained with alizarin red S while being through cell culture.

FIG. 17(B) is an image illustrating the scaffold for hard tissue regeneration prepared in Comparative Example 1 stained with alizarin red S while being through cell culture (14 days).

Figure 17C:
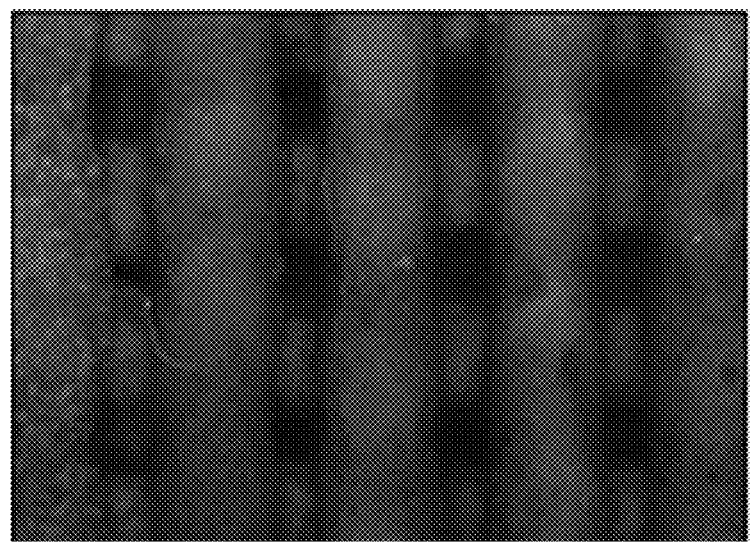
FIG. 17(C) is an image illustrating the scaffold for hard tissue regeneration prepared in Example 2 stained with alizarin red S while being through cell culture.

FIG. 17(C) is an image illustrating the scaffold for hard tissue regeneration prepared in Example 2 stained with alizarin red S while being through cell culture (14 days).

Figure 17D:
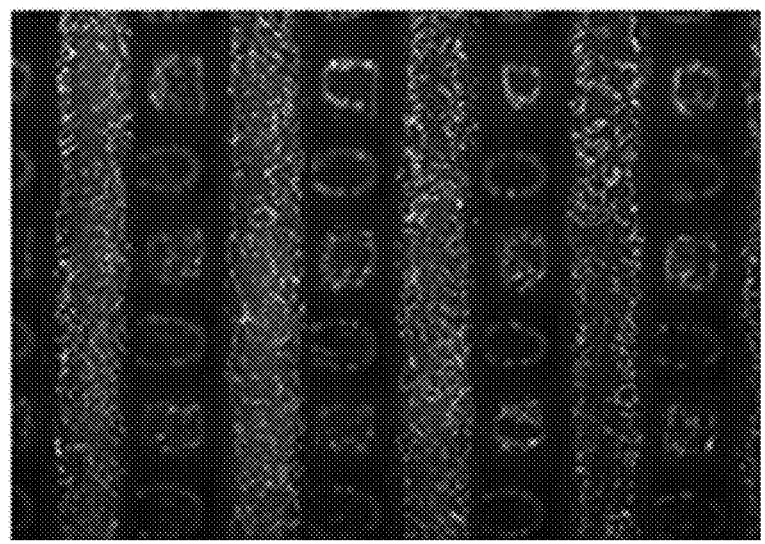
FIG. 17(D) is an image illustrating the scaffold for hard tissue regeneration prepared in Example 1 stained with alizarin red S while being through cell culture.

FIG. 17(D) is an image illustrating the scaffold for hard tissue regeneration prepared in Example 1 stained with alizarin red S while being through cell culture (14 days).

As shown in FIG. 17, the degree of dyeing of alizarin red S was stronger in the scaffold for hard tissue regeneration prepared in Example 1, compared with the scaffold for hard tissue regeneration prepared in Comparative Example 1, suggesting that calcium formation, that is bone mineralization, was accelerated in the scaffold of Example 1.

Experimental Example 7: Evaluation of the Proliferation of Osteoblasts and Osteoclasts According to Drug Release To evaluate the proliferation of osteoblasts and osteoclasts according to drug release from the scaffold for hard tissue regeneration of the present invention, the following experiment was performed.

<7-1> Evaluation of the Proliferation of Osteoblasts

The scaffolds for hard tissue regeneration prepared in Example 1, Example 3, Comparative Example 1, and Comparative Example 2 were sterilized by dipping in 70% ethanol for 1 hour under UV irradiation, which were then washed three times with PBS (Phosphate Buffered Saline). To prevent contamination or pH change during the cell culture, the scaffolds were dipped in cell culture media without MC3T3-E1 cells for a day under the standard culture conditions.

Thereafter, MC3T3-E1 cells were seeded in the scaffolds for hard tissue regeneration at the density of $1.0 \times 10^5$ cells/scaffold, followed by standard culture for 2 hours. Then, the media were added thereto. To eliminate the non-attached cells in the course of the experiment, the media were regularly replaced. 0.1% triton-X was added thereto, followed by further culture for 5 minutes. Then, the scaffolds were washed with 1×PBS. The scaffolds were dipped in 1% BSA (bovine serum albumin) dissolved in PBS for 30 minutes. Phalloidin was added thereto for 45 minutes, followed by washing the scaffolds with 1×PBS. Cell nucleus was stained with DAPI (4',6-Diamidino-2-Phenylindole, Dilactate) for 30 seconds, followed by washing with 1×PBS. After dried, the scaffolds were observed under microscope. The results are presented in FIG. 18.

FIG. 18 is a set of images illustrating the proliferation of osteoblasts (MC3T3-E1) in the presence of the medicinal material released from the scaffold for hard tissue regeneration prepared in each of Example 1, Example 3, Comparative Example 1, and Comparative Example 2.

As shown in FIG. 18, the scaffolds for hard tissue regeneration prepared in Example 1 and Example 3 induced the proliferation of osteoblasts significantly, compared with the scaffolds for hard tissue regeneration prepared in Comparative Examples 1 and 2. Particularly, the scaffolds for hard tissue regeneration prepared in Example 1 and Example 3 had significantly higher density of osteoblasts than the scaffolds for hard tissue regeneration prepared in Comparative Examples 1 and 2.

<7-2> Evaluation of the Proliferation of Osteoclasts

The experiment was performed by the same manner as described in Experimental Example <7-1> except that RAW 264.7 cells, the multinuclear osteoclasts treated with RANKL (Receptor Activation for Nuclear Factor κB Ligand), were used instead of MC3T3-E1 cells, and the results are presented in FIG. 19.

FIG. 19 is a set of images illustrating the proliferation of osteoclasts (RAW 264.7) in the presence of the medicinal material released from the scaffold for hard tissue regeneration prepared in each of Example 1, Example 3, Comparative Example 1, and Comparative Example 2.

As shown in FIG. 19, the scaffolds for hard tissue regeneration prepared in Example 1 and Example 3 inhibited the proliferation of osteoclasts significantly, compared with the scaffolds for hard tissue regeneration prepared in Comparative Examples 1 and 2. Particularly, the scaffolds for hard tissue regeneration prepared in Example 1 and Example 3 had significantly lower density of osteoclasts than the scaffolds for hard tissue regeneration prepared in Comparative Examples 1 and 2, suggesting that the scaffolds for hard tissue regeneration prepared in Example 1 and Example 3 had more excellent inhibitory effect on the proliferation of osteoclasts.

Experimental Example 8: Evaluation of Mechanical Properties

To evaluate the mechanical properties of the scaffold for hard tissue regeneration of the present invention, the following experiment was performed.

First, the scaffolds for hard tissue regeneration (10×10×4 mm) prepared in Example 1, Example 3, Comparative Example 1, and Comparative Example 2 were prepared. Then, the mechanical properties of those scaffolds were measured by using 5 kN load cell (RB Model 302 MLTM; R&B, Korea) and uniaxial testing machine at crosshead speed of 1 mm/min (n=5). Modulus was determined from the stress-strain curve. The results are presented in FIG. 20.

Figure 20:
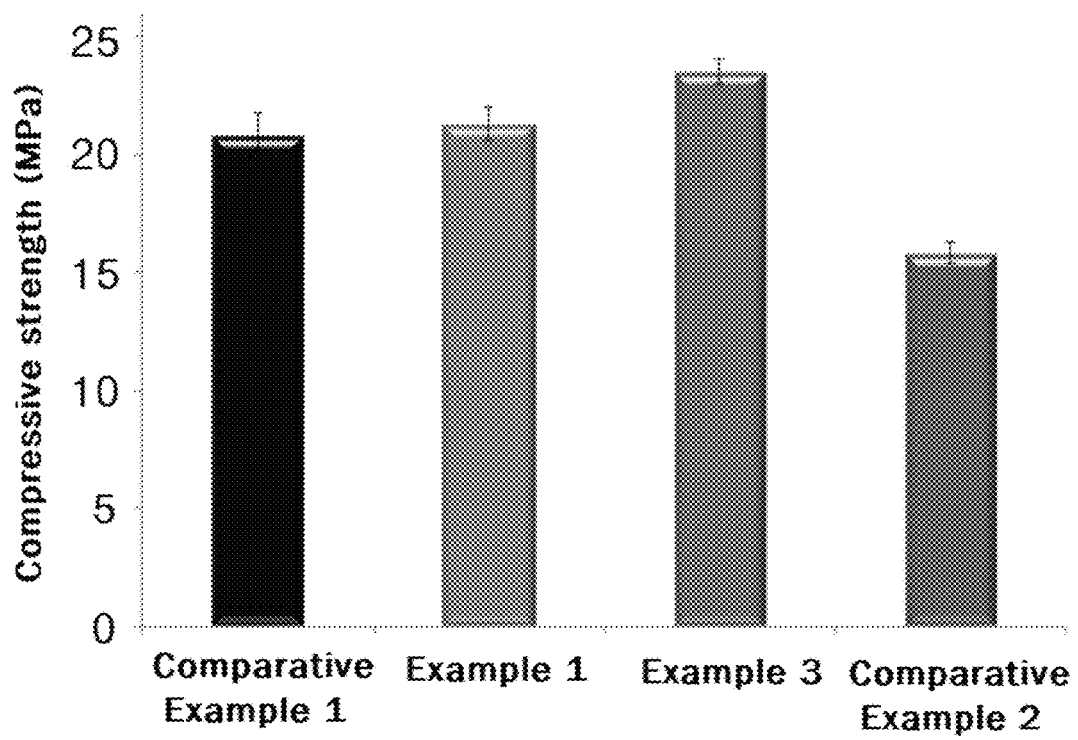
FIG. 20 is a graph illustrating the mechanical properties of the scaffold for hard tissue regeneration prepared in each of Example 1, Example 3, Comparative Example 1, and Comparative Example 2.

FIG. 20 is a graph illustrating the mechanical properties of the scaffold for hard tissue regeneration prepared in each of Example 1, Example 3, Comparative Example 1, and Comparative Example 2.

As shown in FIG. 20, the mechanical properties among the scaffolds of Example 1, Example 3, and Comparative Example 1 were not much different, but the mechanical properties of the scaffolds of Comparative Example 2, which included Alendronate, were poorer than others. That result seemed to be because that Alendronate contained many —OH groups, unlike Quercetein or Genistein, so that phase transition from α-TCP (α-Tricalcium phosphate) into CDHA (Calcium Deficient Hydroxyapatite) was interrupted.

Experimental Example 9: Evaluation of Cement Reaction of the Scaffold by XRD Measurement To evaluate the cement reaction of the scaffold through XRD (X-ray diffraction) measurement, the following experiment was performed.

Phase compositions of α-TCP (α-Tricalcium phosphate) and CDHA (Calcium Deficient Hydroxyapatite) were measured by X-ray diffraction (XRD, DMAX-2200, Rigaku) diffractometry (CuKα1 radiation) operated at 36 kV. The results are presented in FIG. 21.

Figure 21:
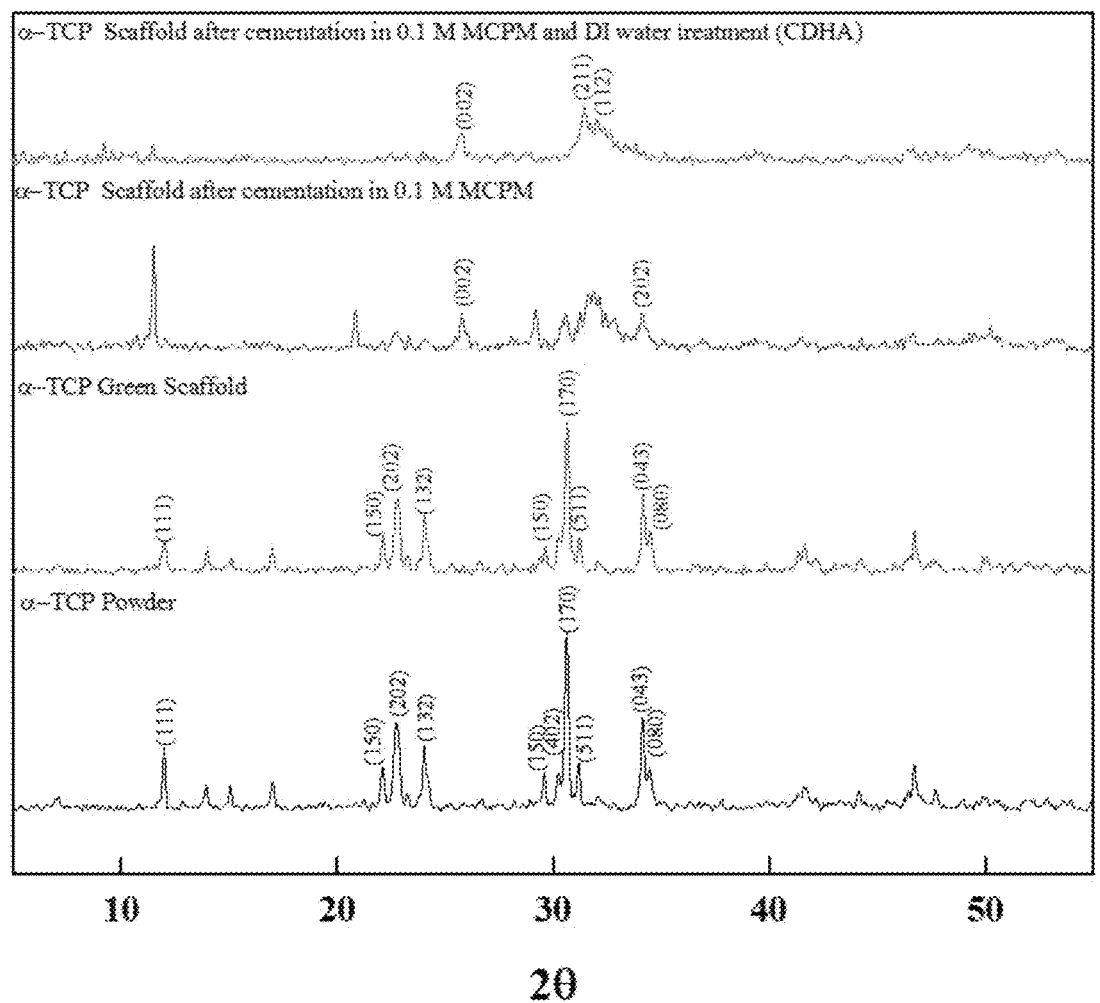
FIG. 21 is a set of images illustrating the cement reaction of the scaffold measured by XRD (X-ray diffraction measurement).

FIG. 21 is a set of images illustrating the cement reaction of the scaffold measured by XRD (X-ray diffraction).

As shown in FIG. 21, hardening into powder like crystal was not observed before the preparation of the scaffold. However, when the scaffold was prepared by using 3D printer and dipped in 0.1 M MCPM (monocalcium phosphate monohydrate), phase transition from α-TCP (α-Tricalcium phosphate) into CDHA (Calcium Deficient Hydroxyapatite) progressed and at last complete phase transition into CDHA was achieved by additional dipping in de-ionized water.

Therefore, the scaffold for hard tissue regeneration of the present invention has less worry of side effects because it uses the polyphenol-based natural substance instead of the conventional bisphosphonate-based osteoporosis treating agent, can improve the osteoblast activity, but at the same time inhibit the osteoclast activity. The scaffold of the invention is advantageous because of the long time sustained-release of the active ingredient such as Quercetein or Genistein, which has been accomplished by dispersing the active ingredient Quercetein or Genistein, which is expected to be able to increase osteogenic activity, evenly in the scaffold.

Experimental Example 10: Evaluation of Biodegradability

To evaluate the biodegradability of the scaffold for hard tissue regeneration of the present invention in the presence or absence of the active ingredient, the following experiment was performed.

The scaffolds for hard tissue regeneration prepared in Example 1 and Comparative Example 1 were dipped in 37° C. PBS (pH 7.4) for 3, 5, 7, 15, 30, 45, and 60 days. Then, the scaffolds were washed with de-ionized water and dried for 2 days at room temperature. The remaining weight of the scaffold for hard tissue regeneration was measured according to the below mathematical formula.

$$\text{Remaining weight (\%)} = 100 - \left[\frac{(Wi - Wd)}{Wi} * 100\right] \quad \text{[Mathematical Formula 1]}$$

In the mathematical formula 1,
Wi is the initial weight of the scaffold; and
Wd is the dry weight of the scaffold after incubation.
The results are presented in FIG. 22.

Figure 22:
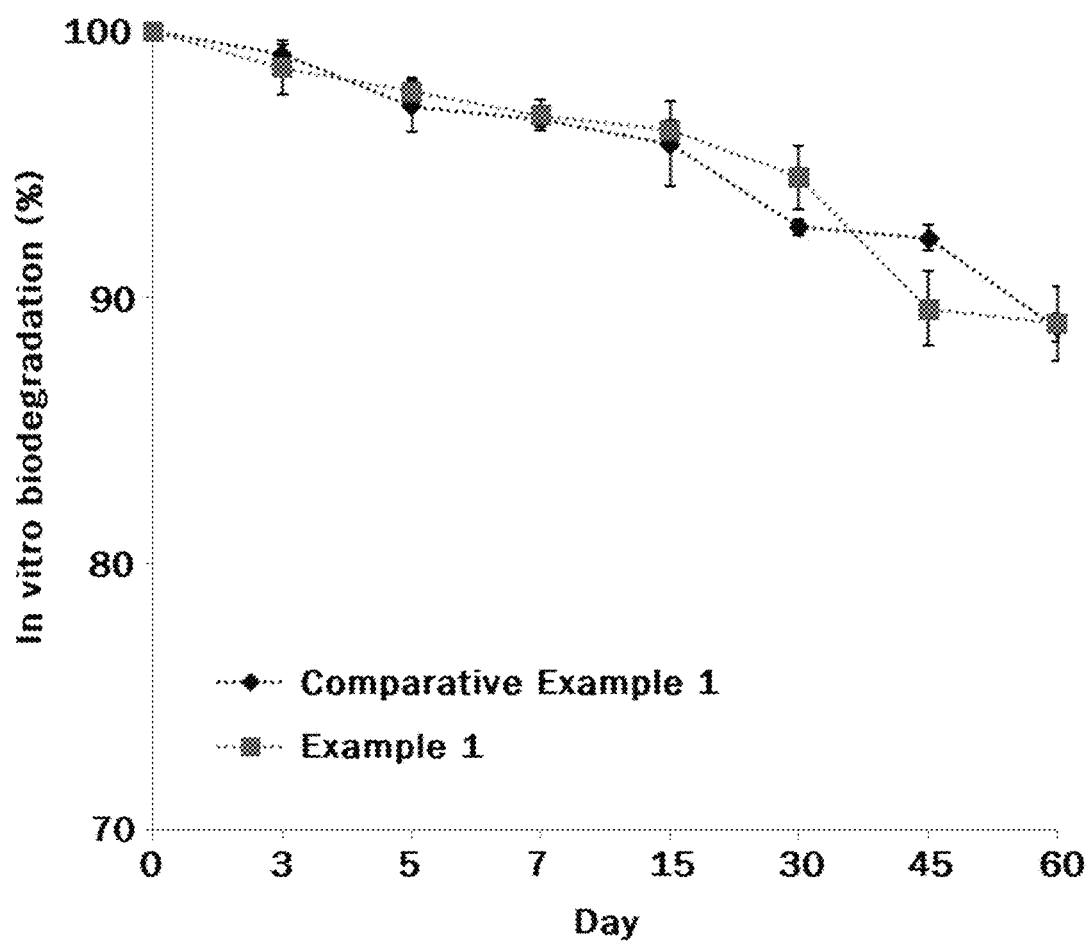
FIG. 22 is a graph illustrating the biodegradation of the scaffold for hard tissue regeneration prepared in each of Comparative Example 1 and Example 1.

FIG. 22 is a graph illustrating the biodegradation of the scaffold for hard tissue regeneration prepared in each of Comparative Example 1 and Example 1.

As shown in FIG. 22, the scaffold for hard tissue regeneration prepared in Example 1 that contained Quercetein demonstrated the similar biodegradability to the scaffold prepared in Comparative Example 1 that did not contain Quercetein, suggesting that the scaffold can be efficiently used as the scaffold for hard tissue regeneration.

INDUSTRIAL APPLICABILITY

The scaffold for hard tissue regeneration of the present invention is prepared by the steps of mixing a polyphenol-based natural substance containing Quercetein or Genistein involved in the activation of osteoblasts and osteoclasts and the biofunctional analogue thereof with a ceramic scaffold material and molding the mixture at room temperature into a three-dimensional scaffold. At this time, the biofunctional material included in the scaffold above is sustain-released slowly over the long period of time so that the osteoblast activity is directly improved and at the same time the osteoclast activity is suppressed in the course of bone regeneration, suggesting that the scaffold of the invention is expected to have the effect of improving bone regeneration.

What is claimed is:

1. A scaffold for hard tissue regeneration comprising quercetin or genistein and calcium phosphate ceramic, wherein the scaffold is configured for implanting in a subject.

2. The scaffold for hard tissue regeneration according to claim 1, wherein the calcium phosphate ceramic is one or more substances selected from the group consisting of α-Tricalcium phosphate (α-TCP), β-Tricalcium phosphate (β-TCP), Hydroxyapatite, Dicalcium phosphate dehydrate (DCPD), Monocalcium phosphate monohydrate (MCPM), Dicalcium phosphate anhydrous (DCPA), and Amorphous calcium phosphate (ACP).

3. A preparation method of the scaffold for hard tissue regeneration of claim 1 comprising the following steps:
   step 1) preparing a powder mixture by pulverizing/mixing a solvent, quercetin or genistein, and calcium phosphate ceramic in ball mill, and drying thereof;
   step 2) preparing a paste by mixing the powder mixture prepared in step 1 with a solvent;
   step 3) molding the paste prepared in step 2 as a three-dimensional scaffold; and
   step 4) inducing bone cement reaction by dipping the three-dimensional scaffold prepared in step 3 in a hardening solution.

4. The preparation method of the scaffold for hard tissue regeneration according to claim 3, wherein the solvents of step 1 and step 2 are independently selected from the group consisting of de-ionized water, phosphate buffered saline (PBS), tetrahydrofurane, dioxane, ethylether, 1,2-dimethoxyethane, methanol, ethanol, propanol, butanol, dimethylformamide, dimethylsulfoxide, dichloromethane, and dichloroethane.

5. The preparation method of the scaffold for hard tissue regeneration according to claim 3, wherein the solvent of step 2 additionally includes one or more thickening agents selected from the group consisting of hydroxypropyl methyl cellulose (HPMC), gelatin, collagen, and alginate.

6. The preparation method of the scaffold for hard tissue regeneration according to claim 3, wherein the three-dimensional scaffold of step 3 is molded by additive manufacturing method.

7. The preparation method of the scaffold for hard tissue regeneration according to claim 3, wherein the hardening solution of step 4 is one or more solutions selected from the group consisting of Mono Calcium Phosphate Mono Hydrate (MCPM), $H_2O$, Phosphate buffered saline (PBS), Diammonium hydrogen phosphate (DAHP), $NH_4H_2PO_4$, $KH_2PO_4$, $K_2HPO_4$, and $NaH_2PO_4$.

8. A preparation method of the scaffold for hard tissue regeneration of claim 1 comprising the following steps:
   step 1) preparing calcium phosphate ceramic powder by pulverizing calcium phosphate ceramic;
   step 2) preparing a paste by mixing the calcium phosphate ceramic powder prepared in step 1 with quercetin or genistein in a solvent;
   step 3) molding the paste prepared in step 2 as a three-dimensional scaffold; and
   step 4) inducing bone cement reaction by dipping the three-dimensional scaffold prepared in step 3 in a hardening solution (step 4).

9. The preparation method of the scaffold for hard tissue regeneration according to claim 8, wherein the solvent of step 2 is one or more solvents selected from the group consisting of de-ionized water, phosphate buffered saline (PBS), tetrahydrofurane, dioxane, ethylether, 1,2-dimethoxyethane, methanol, ethanol, propanol, butanol, dimethylformamide, dimethylsulfoxide, dichloromethane, and dichloroethane.

10. The preparation method of the scaffold for hard tissue regeneration according to claim 8, wherein the solvent of step 2 additionally includes one or more thickening agents selected from the group consisting of hydroxypropyl methyl cellulose (HPMC), gelatin, collagen, and alginate.

11. The preparation method of the scaffold for hard tissue regeneration according to claim 8, wherein the three-dimensional scaffold of step 3 is molded by additive manufacturing method.

12. The preparation method of the scaffold for hard tissue regeneration according to claim 8, wherein the hardening solution of step 4 is one or more solutions selected from the group consisting of Mono Calcium Phosphate Mono Hydrate (MCPM), $H_2O$, Phosphate buffered saline (PBS), Diammonium hydrogen phosphate (DAHP), $NH_4H_2PO_4$, $KH_2PO_4$, $K_2HPO_4$, and $NaH_2PO_4$.

* * * * *